United States Patent [19]

Shindo et al.

[11] Patent Number: 5,587,320
[45] Date of Patent: Dec. 24, 1996

[54] SOLID ORGANIC WASTE PROCESSING APPARATUS

[75] Inventors: Yasuhiro Shindo, Tochigi-ken; Usaburo Yamaguti, Tochigi; Kazuo Ioka, Oyama; Tosio Suzuki, Tatebayashi; Akihiro Minagawa; Syoichi Kitabatake, both of Tochigi-ken, all of Japan

[73] Assignee: Hitachi, Ltd., Tokyo, Japan

[21] Appl. No.: 292,204

[22] Filed: Aug. 19, 1994

[30] Foreign Application Priority Data

Nov. 1, 1993 [JP] Japan ................. 5-273395

[51] Int. Cl.⁶ .................................. C12M 3/00
[52] U.S. Cl. ................... 435/290.1; 435/290.2; 435/290.4
[58] Field of Search ................ 435/290.1, 290.2, 435/290.4

[56] References Cited

U.S. PATENT DOCUMENTS 5,168,727  12/1992  Snellink et al. ................ 62/532

FOREIGN PATENT DOCUMENTS

| 2809344 | 9/1979 | Germany | C05F 9/00 |
|---|---|---|---|
| 3811399 | 10/1988 | Germany | C05F 9/00 |
| 3743651 | 7/1989 | Germany | C05F 9/04 |
| 4021865 | 1/1992 | Germany | C05F 9/00 |
| 4034400 | 4/1992 | Germany | C05F 9/00 |
| 4208390 | 9/1993 | Germany | C05F 17/00 |
| 241671 | 10/1963 | Japan . | |
| 55-121992 | 9/1980 | Japan . | |
| 57-160986 | 10/1982 | Japan . | |
| 57-170183 | 10/1982 | Japan . | |
| 60-131888 | 7/1985 | Japan . | |
| 1-145388 | 6/1989 | Japan . | |
| 79101850 | 3/1981 | Taiwan . | |
| 204638 | 4/1993 | Taiwan | C05F 9/02 |

*Primary Examiner*—David A. Redding
*Attorney, Agent, or Firm*—Antonelli, Terry, Stout & Kraus

[57] ABSTRACT

An apparatus for processing solid organic waste by crushing and/or agitating and fermenting the waste includes a solid organic matter processing device including a processing vessel provided with a crushing unit for receiving and crushing the solid organic waste and a processing unit for agitating and fermenting the crushed waste, a heat exchanger disposed outside the solid organic matter processing device which heat exchanger condenses vapor in a gas supplied from the processing vessel of the solid organic matter processing device to thereby change the vapor to liquid and to discharge the liquid, and gas circulation pipes for providing a gas circulation path through which the inside of the processing vessel of the solid organic matter processing device is operably connected to the heat exchanger and through which a gas in the processing vessel of the solid organic matter processing device is supplied into the heat exchanger and almost all of which gas processed in the heat exchanger is returned to the solid organic matter processing device while a portion of the gas processed in the heat exchanger or a portion of the gas supplied from the processing vessel of the solid organic matter processing device is discharged to the outside of the apparatus.

30 Claims, 9 Drawing Sheets

SOLID ORGANIC WASTE PROCESSING APPARATUS

BACKGROUND OF THE INVENTION

1. Field of the Invention

The present invention relates to a solid organic waste processing apparatus, and more specifically, to a solid organic waste processing apparatus for processing solid organic waste as a whole such as kitchen waste (kitchen garbage), waste dumped in towns, waste generated in a food manufacturing process, biomass and the like by aerobic fermentation, and this apparatus can be widely applied to a home use, business use and public use and further used in an industrial scale.

2. Description of the Related Art

Recently, a technology for processing solid organic waste by aerobic fermentation or a technology for making waste to compost is evaluated again because it is not only a processing method by which no pollution is caused but also a technology for reusing waste and returning waste to nature.

In particular, as a stock breeding industry which has consumed a large amount leftover rice is declined, the development of a processing apparatus is desired which is capable of processing kitchen waste or so-called kitchen garbage, while solving odor pollution, at a high speed and a high decomposition ratio is desired.

Conventionally, most of solid waste such as waste generated from agriculture, sludge generated from a sewer system, and the like is made to compost by causing it to naturally ferment in such a manner that it is left on a field for a long time without positively managing it.

On the other hand, examples of development by which fermentation is accelerated by agitating waste by the use of a fermentation apparatus or partially managing the supply of oxygen are increased. For example, Japanese Patent Unexamined Publication No. 1-145388 and the like are known as the examples.

Nevertheless, in the conventionally developed processing apparatuses, when waste containing a large amount of water such kitchen waste and the like is processed at a high speed by fermentation carried out at a high temperature, an assistant raw material such as sawdust, rice hulls and the like serving as a water content adjustment material must be added in addition to a raw material. If the raw material is processed as it is, since it has an average water content of 80%, water exists excessively in the process in which the material is processed, and thus the raw material cannot be fermented. When the assistant raw material is to be added, a problem arises in that not only it must be stably obtained but also a processing efficiency of the raw material is lowered by an amount of the added assistant raw material and a volume of resulting compost is increased.

Further, since the conventional processing apparatuses employ a so-called batch system, when waste is charged once, next waste cannot be charged until a predetermined processing time has elapsed. Thus, these apparatuses are very inconvenient as a waste processing apparatus for processing continuously generated waste.

Further, since the conventional apparatus pay no attention to a problem of environmental pollution, they scatter a bad odor and a lot of vapor to surroundings.

SUMMARY OF THE INVENTION

A solid organic waste processing apparatus for processing solid organic waste by crushing and/or agitating and fermenting the waste of the present invention has a solid organic matter processing device including a processing vessel provided with a crushing unit for receiving and crushing the solid organic waste and a processing unit for agitating and fermenting the crushed waste, a heat exchanger disposed outside the solid organic matter processing device for condensing vapor in a gas supplied from the processing vessel of the solid organic matter processing device, changing the vapor to liquid and discharging the liquid, and a gas circulation means for forming a gas circulation path by which the inside of the processing vessel of the solid organic matter processing device is operably connected to the heat exchanger and through which a gas in the processing vessel of the solid organic matter processing device is supplied into the heat exchanger and almost all of the gas processed in the heat exchanger is returned to the solid organic matter processing device and further discharging a portion of the gas processed in the heat exchanger to the outside of the apparatus or a portion of the gas supplied from the processing vessel of the solid organic matter processing device to the outside thereof.

It is preferable that the processing apparatus of the present invention further includes a deodorization processing unit for deodorizing at least a portion of a gas supplied from the processing vessel and discharging a deodorized gas to the outside air and/or deodorizing at least a portion of a gas processed by the heat exchanger and discharging a deodorized gas to the outside air.

The processing apparatus of the present invention may further include a liquid purification unit for neutralizing water produced in a process carried out by the heat exchanger, neutralized water produced by the liquid purification unit is supplied to the deodorization processing unit and the organic matter contained in the neutralized water is removed by the deodorization processing unit as well as the neutralized water is used to keep the water in the deodorization processing unit to a predetermined level.

It is preferable that the processing apparatus of the present invention supplies a portion of the gas processed by the heat exchanger to the crushing unit or the vicinity of the crushing unit and promotes the dehydration of crushed solid organic waste.

The processing apparatus of the present invention can connect the extreme ends of a plurality of the agitation arms by a connecting member so that the connecting member promotes an agitating operation carried out in the processing vessel and prevents solid organic waste from adhering to the processing vessel.

The processing apparatus of the present invention includes a control unit for stopping the operation thereof after a predetermined period of time and continuously operating only the gas circulation means so that the apparatus is adapted to an unused state for a long period.

Condensed liquid may be discharged through a drain pipe disposed to a path for returning the heat-exchanged gas to the processing vessel, comb-shaped fixed arms are disposed on the sides or bottom of the processing vessel in the crushing unit, agitation arms are mounted on a rotary shaft in the crushing unit and processing unit, respectively, the rotary shaft passing through the processing unit from the crushing unit, and each of the agitation arms located in the crushing unit passes between adjacent ones of the fixed arms in such a manner that it is about to be in contact with the fixed arms when rotated to have a function for crushing solid organic waste.

Further, the gas circulation means includes a path for returning the heat-exchanged gas to the processing vessel, a circulation fan disposed in the path for circulating the gas to the processing vessel and a path for supplying the gas in the processing vessel to the heat exchanger, and a means for taking outside air into the heat exchanger may be provided, when necessary.

Although the above processing vessel may be composed of a single vessel, it is preferable that the vessel is subdivided into a plurality of multi-staged vessels to reduce the size of the apparatus as a whole. When the vessel is subdivided into the plurality of vessels, it is preferable that the uppermost vessel is composed of a processing vessel having a crushing unit provided with a charge port of solid organic waste and a processing unit and a lower vessel is composed of a processing vessel mainly composed of a processing unit, and moreover matters to be processed overflow the end plates of the respective processing vessels. Then, a storing unit is disposed in the vicinity of the end plate of the final stage vessel so that processed matters (made of dry powder) overflowing the end plate is recovered to the storing unit. When a predetermined amount of the processed matters is recovered, the storing unit can be taken out to the outside by opening a discharge gate.

Further, an intermediate partition(s) may be disposed at least in the processing unit(s) of the processing vessel(s) to separate the inside of the processing vessel(s) to substantially a plurality of vessels to provide a dam effect to the matters to be processed.

Further, to describe the configurational arrangement of the agitation arms to be mounted on the rotary shaft, the agitation arms in the crushing unit are formed to a polygonal bar shape (including circular shape and ellipse shape) and are preferably disposed very near to comb-shaped fixed arms disposed on the bottom of the processing vessel so that the agitation arms are about to be in contact with the fixed arms in order to increase a crushing effect.

The agitation arms in the processing unit may be mounted on the rotary arm vertically with respect to the rotation axis thereof but they may be inclined by a predetermined angle so that matters to be processed do not stay on the bottom of the processing unit but are swung. When the agitation arms are mounted vertically with respect to the rotary arm, they are generally formed to a bar shape, strip shape, or bar shape or strip shape each having a different width at the upper and lower ends thereof and these agitation arms are radially disposed around the rotary shaft. Further, when the agitation arms are inclined with respect to the rotary arm, they may be further formed to a disk shape. As shown in FIG. 16, a plurality of the agitation arms are preferably mounted on the rotary arm by being continuously dislocated with respect to an circumferential direction by a predetermined angle (preferably in the range of 30°–90°). With this arrangement, when the agitation arms are rotated, solid organic waste is moved from the crushing unit.

A heating means is disposed on the outside wall of the processing vessel, for example, on the bottom of the vessel and since the processing vessel is usually heated to 50°–80° C., when matters to be processed stay on the bottom of the vessel, they are baked and adhered to the bottom of the vessel in a paste state and lower thermal transmission. Therefore it is effective to swing the matters to be processed by the agitation arms.

The heating mean disposed on the processing vessel has a U-shaped sheath heater or a plate-shaped heater. The plate-shaped heater is preferable because it can uniformly heat a vessel wall. In any way, it is important that heat is applied and maintained so that fermentation is sufficiently carried out in the processing unit and a temperature is preferably controlled by a thermostat for the adjustment of temperature.

To describe the direction in which the agitation arms are rotated in the processing vessel and a rotation schedule, although they may be rotated in a predetermined direction continuously or intermittently, it is more effective that they are driven in the three sequences of forward rotation, stop and backward rotation for a predetermined period of time, respectively. Further, the processing vessel is formed to a rectangular box-shape having a bottom portion obtained by connecting in parallel two curved bottom surfaces each having arc-shaped cross section and includes two rotary shafts each disposed in the longitudinal direction of the processing vessel at the center of the arc of each of the curved bottom surfaces, fixed arms planted on the wall surface of the processing vessel so as not to interfere with the agitation arms, and a partition for separating a crushing unit from a processing unit, and the position where the two curved bottom surfaces are connected is located lower than the rotary shafts.

Further, there may be provided a condensed liquid purification unit including an adjustment tank and a processing tank. The adjustment tank is filled with a weak alkaline material (for example, limestone etc.) for neutralizing liquid passing therethrough and the processing tank is filled with a carrier to which microorganisms for removing an organic matter in the liquid are fixed.

The deodorization processing unit may include a deodorizing tank which is filled with liquid (for example, water) with which mixed is a carrier having microorganisms fixed thereto and disposed downward of an adjustment tank and a water level tank (870) having a discharge pipe (880) positioned at the same location as the liquid level of the deodorizing tank (840) and disposed downward of the deodorizing tank (840), the above microorganisms being similar to those used in the condensed liquid purification unit.

The processing apparatus of the present invention may include a storage tank (250) for storing processed discharging matters which is connected to the downstream side of a solid organic matter processing device (A) through a connection pipe (240) having a blower (245), a water storage tank (270) connected to a liquid purification unit through a connection pipe and a sprinkling means (275, 280, 290).

A feature of the present invention is to effectively remove water which is contained in kitchen garbage in an average amount of about 80%, to effectively crush matters to be processed which are contained in the fermentation vessel (processing vessel) through the crushing unit, mixing these matters with species of bacteria so that they are sufficiently fermented by species of aerobic bacteria in the processing unit and dried.

The inside of the processing vessel is arranged to be kept to a temperature of, for example, 50°–80° C. at which fermentation can be sufficiently carried out by species of aerobic bacteria, and specifically there are provided an air taking out pipe for taking out air from the processing vessel, an air return pipe for returning air to the processing vessel and a heat exchanger connected to the air taking out pipe and air return pipe. If desired, an air supply means may be provided to take in outside air and supplying the same to the heat exchanger.

By adoping the constitution, steam generated in the processing vessel by the heating therein passes the air-taking-out pipe and enters a plurality of cooling tubes which the heat exchanger comprises. In the heat exchanger there are used the cooling tubes each having a large diameter such as, for example, 18 mm in the example of the present invention so that the cooling tubes may not be clogged by the fine particles of the processed matters. Thus, regarding the steam flowing therethrough, a part of the steam flowing along and in the vicinity of the inner diameter surface of each of the cooling tubes is cooled to be condensed to water, and another part of the steam flowing along the center portion of each of the cooling tubes returns into the processing vessel through the air return pipe without being condensed. The condensed water become liquid droplets and is discharged outward of the apparatus through a drain pipe.

The steam returned into the processing vessel through the air return pipe acts to keep such a necessary level of moisture that sufficient fermentation occurs by species of aerobic bacteria. The steam is circulated between the processing vessel and the heat exchanger, and a state of high moisture is maintained until water is substantially completely removed.

Thus, in comparing the apparatus of the present invention with prior art apparatus in which there is no circulation system between a heat exchanger and a processing vessel, although in the prior art apparatus the water in the processing vessel is quickly removed outwardly and becomes substantially zero or is in a very low level, in the apparatus of the present invention the steam and a high level of moisture are maintained in the processing apparatus for a long period of time, which steam and high level of moisture can bring about a very favorable condition for the fermentation generated by the aerobic bacteria. Namely, both of the heat exchanger and the circulation constitution comprising the air-taking-out pipe and the air-return pipe in the present invention act to realize at the same time both respects, which apparently contradict each other, that the water is removed for reducing the weight of matter to be processed and that the moisture in the processing vessel is maintained in such a necessary level as the sufficient fermentation can occur by the action of the aerobic bacteria.

Further, in the apparatus of the present invention there are provided a deodorizing communication pipe in a part of the air-returen pipe, a deodorizing device communicated with the deodorizing communication pipe, and an air-discharing pipe communicated with the deodorizing device, so that molecules of a sickly odor are decomposed by bacteria received in the deodorizing device and gas substantially having no odor is discharged. Otherwise, a portion of the air from which water is removed may be directly exhausted. Since the pressure in the processing vessel is lowered in proportion to an amount of the exhausted air, fresh air flows thereinto from a separately provided air intake port. Note, an amount of taken air corresponds to air required (consumed) when matters to be processed are fermented in the processing unit.

When this process is cyclicly repeated, water is effectively and continuously removed from the air in the processing vessel and odor is removed from exhausting air as well as fresh air flows into the processing vessel so that aerobic fermentation can be continuously carried out.

Regarding the adjustment of water contained in the waste received in the processing vessel, an intermediate partition plate disposed in the processing vessel acts in a manner explained below. That is, when the waste in the processing vessel becomes light in weight by the reduction of the water, the waste moves boyond the partition plate to thereby falls into an adjacent vessel. Thus, by setting the intermediate partition plate to have a proper level of height, the waste is maintained in the processing vessel while the waste has a minimum water level necessary for the waste to be fermented, and the waste is moved into the adjacent vessel when the water contained in the waste is reduced to be less than the minimum water level, that is, the intermediate partition plate has a function for automatically adjusting water.

Another feature of the present invention is to use the processing vessel for a plurality of objects and maximize the space factor of the apparatus by taking the disposition of components into consideration so that the apparatus is made compact with excellent cost performance.

More specifically, the processing vessel executes the four functions in total of (1) crushing kitchen garbage, (2) mixing charged kitchen garbage with fermentation bacteria, (3) supplying air to the fermentation bacteria, and transferring matters to be processed from an upstream side to a downstream side.

More specifically, when kitchen garbage is charged in to the processing vessel from a waste charge port in the state that fermentation bacteria (species of aerobic bacteria) is previously prepared at the lower portion of the processing vessel, first, the charge garbage is held between the agitation arms and the fixed arms extending from the bottom of the vessel and crushed by them in the crushing unit located below the waste charge port as the agitation arms rotate, then the garbage is mixed with the fermentation bacteria as the agitation arms rotate. At the same time, air is supplied to the fermentation bacteria by agitation.

When the kitchen garbage is charged from the waste charge port, the garbage overflows, and when a partition is provided, overflown garbage flows into the next region from the upper portion of the partition and further overflows an end plate and drops and flows into a discharging matter storing unit and transferred. When the apparatus has tow-staged processing vessels and no partition is provided, matters to be processed overflow the end plate of the upper stage processing vessel and drops into the lower stage processing vessel.

This disposition is very rational and has an excellent space factor and thus the apparatus can be made compact with an excellent cost performance.

In a case where the apparatus has the two rotary shafts and the connecting portion where the two curved bottom surfaces are connected each other is located below the rotary shafts, the processing capacity of the processing vessel can be increased, matters to be processed being frequently transferred in the vessel and an area where fermentation bacteria are mixed and to which air is supplied is increased.

When the solid organic matter processing device is assembled separately from a gas and liquid processing device and they are assembled in a final process or at a site where the apparatus is installed, the assembly and transportation of the apparatus can be rationalized.

DESCRIPTION OF THE PREFERRED EMBODIMENTS

Embodiment 1

Figure 1:
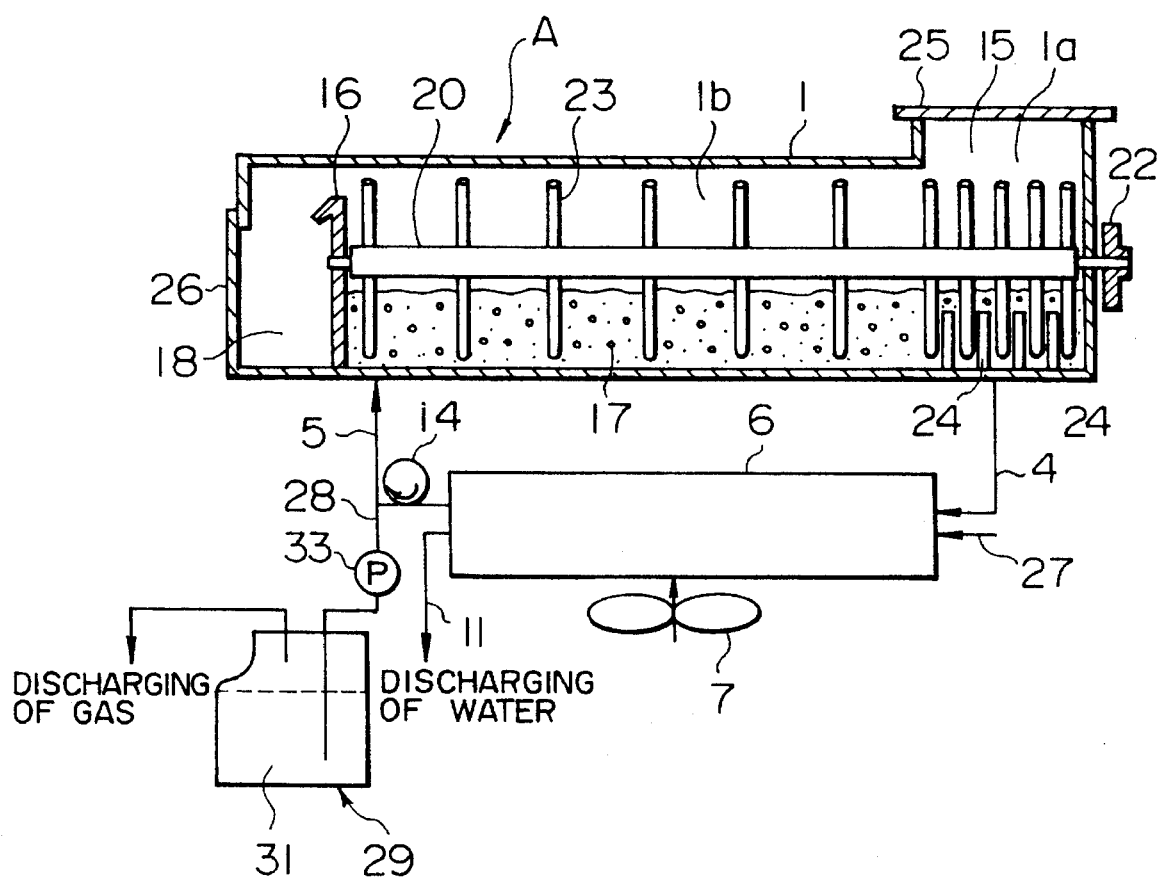
FIG. 1 is a schematic diagram partially in cross section of an embodiment of a solid organic waste processing apparatus of the present invention.

FIG. 1 is a schematic diagram showing an example of a processing apparatus of the present invention having a processing vessel arranged as a box-shaped single vessel, wherein the processing vessel 1 has a crushing unit 1a and a processing unit 1b. The crushing unit 1a has a comb-shaped fixed arm 24 fixed to the bottom of the vessel and the processing unit 1b has an end plate 16 disposed at the terminal end thereof. A waste charge port 15 is disposed on the crushing unit 1a of the processing vessel 1 in such a manner that it can be opened and closed when necessary. A discharging matter storing unit 18 is disposed adjacent to the end plate 16 of the processing unit 1b and further a discharge gate 26 for taking out the storing unit 18 constitutes a portion of the outside wall provided with the wall surface of the processing vessel 1.

Further, a rotary shaft 20, which extends through the crushing unit 1a and processing unit 1b and has an end connected to a drive means 22, is disposed at the center of the processing vessel and a plurality of agitation arms 23 are fixed radially to the rotary arm 20 at predetermined intervals. A heater 13 as a heating means is disposed on the outside wall of the bottom of the processing vessel so that the processing vessel is kept to a temperature at which waste can be effectively and sufficiently fermented.

A heat exchanger 6 is connected to the crushing unit 1a and processing unit 1b of the processing vessel 1 through an air intake pipe 4 and an air return pipe. The heat exchanger 6 comprises a plurality of cooling tubes, at a high temperature side of which heat exchanger 6 an air intake port 27 is opened to the surrounding atmosphere. On the other hand, a drain pipe 11 is disposed on the low temperature side of the heat exchanger 6 to discharge water produced from vapor condensed by exchanging the heat thereof, a circulation fan 14 being disposed in the midway of the air return pipe 5 to forcibly return air to the processing unit 1b. Therefore, a gas in the processing vessel is circulated through the air intake pipe 4, heat exchanger 6 and air return pipe 5 which serve as a circulation system, and a suitable amount of fresh air is taken into the circulation system through the air intake port 27 in the midway of the circulation system to effectively promote fermentation in the processing unit 1b. The heat exchanger 6 is cooled by air supplied from a blower 7.

A deodorizing communication pipe 28 is branched from the air return pipe 5 between the circulation fan 14 and the processing unit 1b, and a pump 33 is disposed in the midway of the deodorizing communication pipe 28. The pump 33 supplies a gas to a deodorization processing unit 29 under a predetermined pressure and causes the gas to be blown into a deodorizing vessel 31 filled with active sludge so that the deodorization processing unit 29 carries out a deodorizing process and exhausts a deodorized air to the outside. An amount of air exhausted to the outside substantially corresponds to air taken in through the air intake port 27, that is, to air consumed by the fermentation in the processing vessel 1.

A charge gate 25 is disposed on the waste charge port 15 of the processing vessel 1 and the discharge gate 26 is provided with the discharging matter storing unit 18, respectively to separate the inside of the vessel from the outside air to prevent the dispersion of heat and odor.

An operation mechanism of this apparatus will be described. First, kitchen garbage is charged from the waste charge port 15 of the processing vessel 1, solid matters are finely crushed by the crushing unit 1a and sequentially transferred to the processing unit 1b. The processing unit 1b is filled with a predetermined amount of species of aerobic bacteria collected from compost, only when the apparatus is operated for the first time. Crushed organic matters to be processed are fermented in the processing unit 1b by the aerobic species and decomposed. To promote fermentation and decomposition, the processing vessel is kept at a suitable temperature of 50°–80° C. at all times by the thermostat (not shown) of the heating means 13. When a predetermined amount of the processed matters (compost) are accumulated in the vessel, they overflow the end plate 16 and drop into the storing unit 18 to be recovered therein, and then taken out to the outside by opening the discharge gate 26.

A gas circulation system for connecting the inside of the processing vessel 1 with the heat exchanger 6 will be described below. A gas of high temperature and high humidity (mainly composed of air with an odor) is taken into the high temperature side of the heat exchanger 6 from the crushing unit 1a through the air intake pipe 4. At this time, a predetermined amount of fresh air is taken from the air intake port 27 into the circulation system. In the heat exchanger 6 there are used cooling tubes each of which has a considerably large inner diameter such as, for example, 18 mm in the example so that the tubes is prevented from being clogged by fine particles of the waste, with the results that a part of the steam flowing along and in the vicinity of the inner diameter surface of each of the cooling tubes is cooled to be condensed to water, and that another part of the steam flowing along the center portion of each of the cooling tubes returns into the processing vessel 1 through the air return pipe 5 without being condensed. The condensed water becomes liquid droplets and is discharged outward of the apparatus from the low temperature side of the heat-exchanger 6 through a water discharge pipe 11. Further, an amount of air corresponding to air taken into the circulation system from the air intake port 27 is exhausted with the odor thereof removed by the deodorization processing unit 29. Thus, the inside of the circulating system is kept to a state substantially near to the atmospheric pressure at all time.

Since this apparatus is arranged to have a relatively small size and since waste can be continuously charged into the apparatus, the apparatus can be easily operated and maintained, when it is applied to the industrial fields such as a food processing industry, food service industry and the like where kitchen garbage is generated at all times. The apparatus is advantageous in that it can process waste without depending upon waste collectors and be installed near to the location where waste is generated because surroundings are not adversely affected by the apparatus. Further, since compost is almost odorless dry powder with a very high added value and can be recovered as manure for raising farm products, garden plants, other general plants, this apparatus is preferable from the view point of the reuse of waste.

Embodiment 2

This embodiment shows another apparatus of the present invention having two-staged processing vessels. The embodiment will be described below with reference to FIG. 2 and FIG. 3. FIG. 3 is a side view of the apparatus in the state that an outside box is removed and FIG. 3 is a backside view of the apparatus when viewed from a P direction of FIG. 2. The arrangement of the apparatus will be described with reference to the figures. Numeral 1 denotes a processing vessel which is formed to a horizontally long box shape and has an upper state processing vessel a and a lower stage processing vessel 3.

Numeral 4 denotes an air intake pipe for taking air from the upper state processing vessel 2, and numeral 5 denotes an air return pipe for returning air to the lower state processing vessel 3. The air intake pipe 4 and air return pipe 5 are disposed outside the processing vessel 1 and connected to a heat exchanger 6 disposed outside the processing vessel 1 in the same way.

Numeral 7 denotes an air supply means for taking outside air into the heat exchanger 6 and supplying the same. The heat exchanger 6 has a vertical and cylindrical inlet pipe 8 to be connected to the air intake pipe 4, a vertical and cylindrical outlet pipe 9 to be connected to the air return pipe 5 and a plurality of cooling tubes 10 extending in a substantially horizontal direction and connected to the inlet pipe 8 and outlet pipe 9.

A drain pipe 11 is disposed below the outlet pipe 9 and has a water discharge hole 12 opened to the outside at a lower portion of the apparatus.

The processing vessel 1 has a heating means 13 and a temperature keeping means (not shown) and a temperature is controlled by a thermostat so that the inside of the processing vessel 1 is kept at 50° C.–60° C. at all times.

A circulation fan 14 is disposed in the midway of the air return pipe 5 to circulate air in the processing vessel 1 to the heat exchanger 6.

Figure 3:
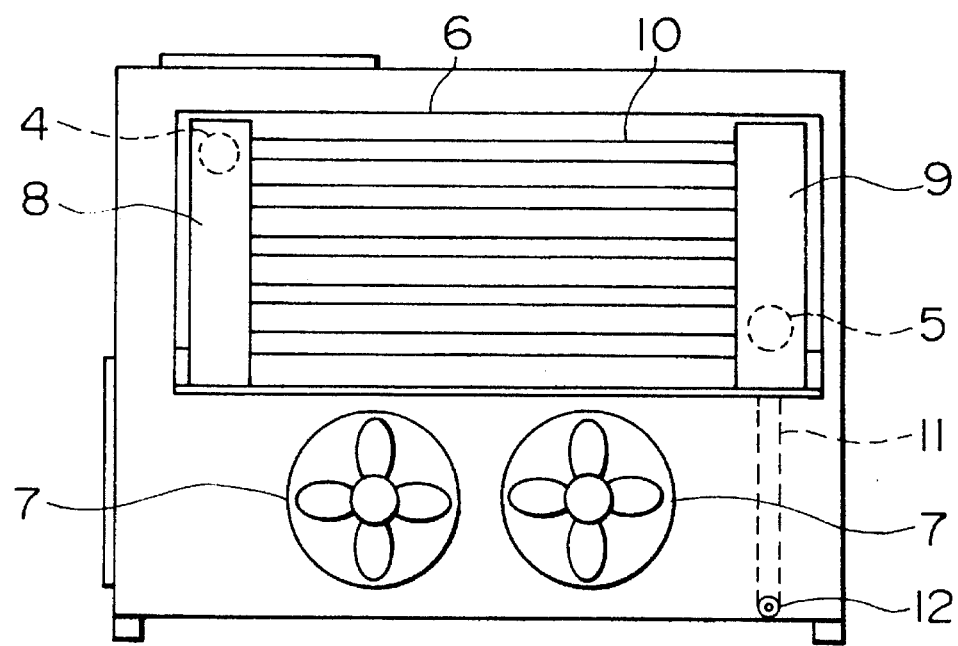
FIG. 3 is a backside view of the solid organic waste processing apparatus when viewed from a P direction of FIG. 2.
Figure 4:
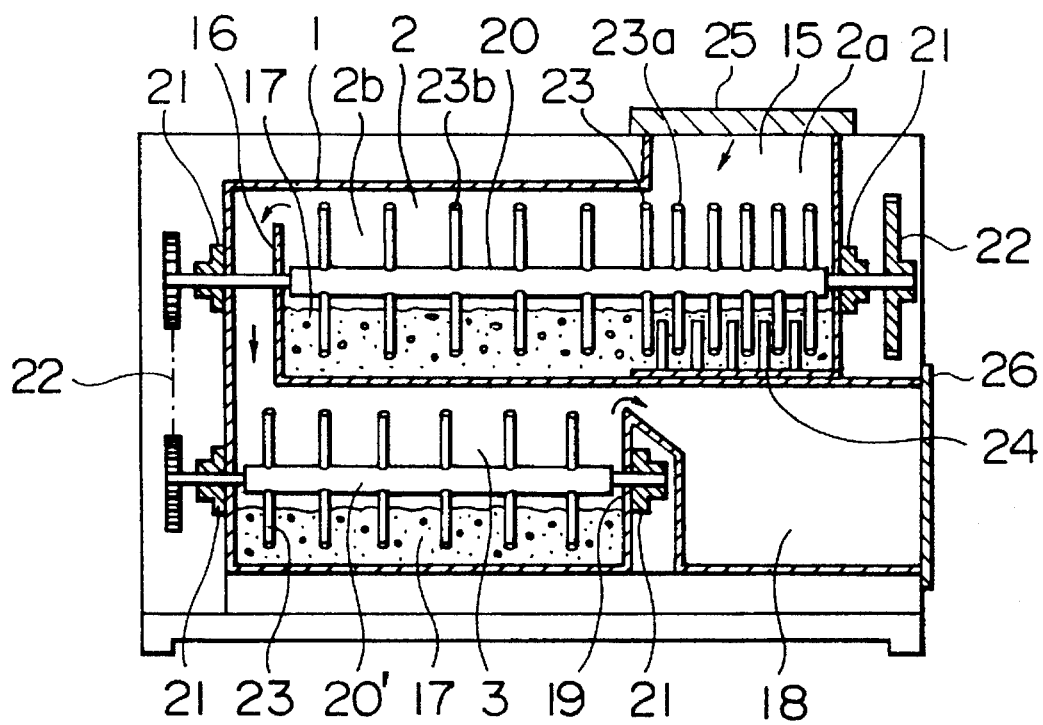
FIG. 4 is a front longitudinal cross sectional view of the main part of the solid organic waste processing vessel.

FIG. 4 shows a front vertical cross sectional view of the main part of the processing vessel 1, in which a right and left side are reversed to those shown in FIG. 3 (backside view). The arrangement of the processing vessel 1 will be described with reference to FIG. 4 in more detail.

The function of the upper stage processing vessel 2 can be divided to a crushing unit 2a and a processing unit 2b adjacent to it from the function thereof. A waste charge port 15 is disposed on the crushing unit 2a and an upper end plate 16 is disposed to the end of the processing unit 2b on the opposite side of the waste charge port 15. This upper end plate 16 has a function as a dam for storing a predetermined amount of matters to be processed in the processing unit 2b and a level at which the matters to be processed are overflown to the lower stage processing vessel 3 can be adjusted by suitably selecting the height of the upper end plate 16.

Species of bacteria 17 for fermentation are prepared on the bottoms of the upper stage processing vessel 2 and lower stage processing vessel 3, respectively. Note, the preparation of the species of bacteria 17 is needed only when the apparatus is operated for the first time, and when the apparatus is operated steady, there are always exist an sufficient amount of aerobic bacteria which proliferate by themselves. Thus, the species of bacteria 17 need not be newly prepared.

A discharging matter storing unit 18 having a length corresponding to the difference between the upper state processing vessel and the lower stage processing vessel is disposed under the upper stage processing vessel 2 (more specifically, under the crushing unit 1a) and a lower end plate 19 is disposed on the discharged matter storing unit 18 side of the lower stage processing vessel 3.

The upper stage processing vessel 2 is provided with a rotary shaft 20 and bearings 21 and the lower stage processing vessel 3 is provided with a rotary shaft 20' and bearings 21 and further a driving means 22 is provided to drive the rotary shaft 20, 20'. Each of the rotary shafts 20, 20' is provided with a plurality of agitation arms 23. Further, fixed arms 24 extending from the bottom of the vessel are disposed in the crushing unit 2a located below the waste charge port 15 of the upper stage processing vessel 2 and each fixed arm 24 is located between each pair of the plurality of agitation arms 23.

Charged wastes are held between the agitation arms 23a in the crushing unit 2a and the fixed arms 24 and crushed therebetween and further gradually pushed and flown into the processing unit 2b and mixed with the species of bacteria 17 prepared on the bottom of the vessel by the rotation of the agitation arms 23b.

The matters to be processed which have been gradually pushed and flown by charged waste overflow the upper end plate 16 of the upper stage processing vessel 2 and drop into the lower stage processing vessel 3. The portion of the matters which have not been sufficiently fermented is perfectly fermented in the lower stage processing vessel 3. The matters to be processed caused to flow through the processing vessel 3 overflow the lower end plate 19 of the processing vessel 3 and drop into the discharging matter storing unit 18 and recovered as useful powder compost.

A charge gate 25 is disposed on the waste charge port 15 of the processing vessel 2 and a discharge gate 26 is disposed to the discharging matter storing unit 18 of the lower processing vessel 3 to separate the inside of the vessels from the outside air to prevent the dispersion of heat and odor.

Figure 2:
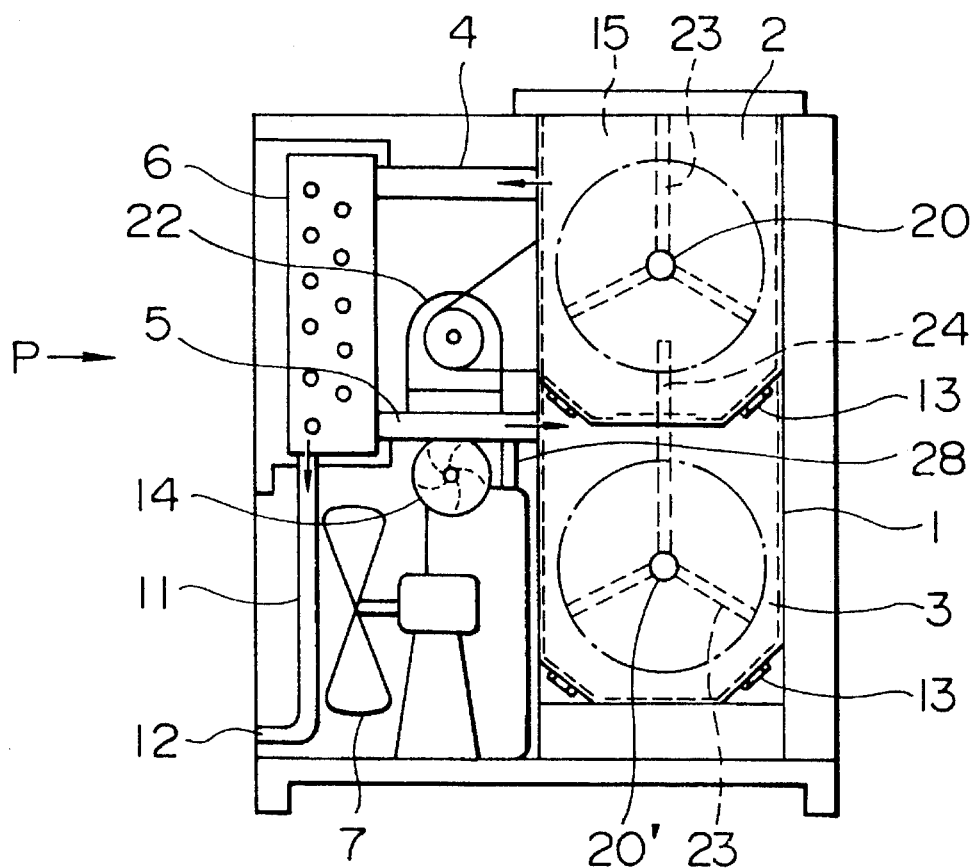
FIG. 2 is a side view of another embodiment of the solid organic waste processing apparatus of the present invention in the state that an outside box is removed.
Figure 5:
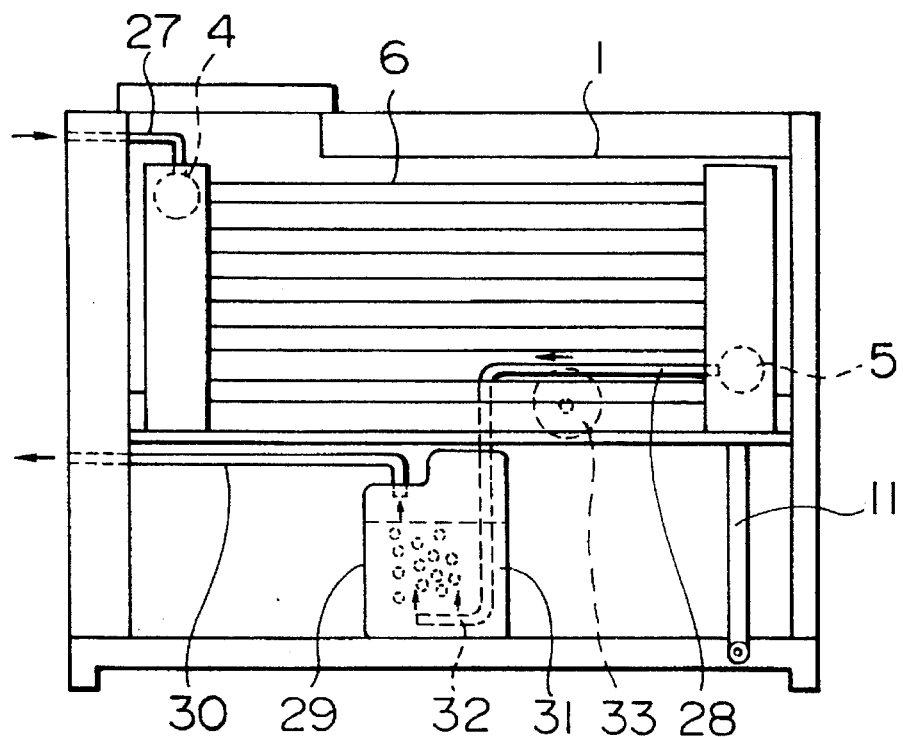
FIG. 5 is a backside view of the solid organic waste processing apparatus when viewed from the P direction of FIG. 2 in the state that an outside box and an air supply means are removed.

FIG. 5 shows a backside view of the processing apparatus viewed from the direction P of FIG. 2 in the same way as FIG. 3 in which an outside box and air supplying means are removed. This figure mainly explains the relationship of piping for connecting the heat exchanger 6 to the processing vessel 1 and an example of arrangement of a deodorization processing unit 29 in detail.

An air intake port 27 for taking fresh air is disposed in the midway of a path interconnecting the air intake pipe 4 and air return pipe 5 and heat exchanger 6 connected to them.

A deodorizing communication pipe 28 is disposed to a part of the air return pipe 5 (connected to the low temperature side of the heat exchanger 6) between the processing vessel 1 and the circulation fan 14 (refer to FIG. 2) and the deodorization processing unit 29 is connected to the deodorizing communication pipe 28. An air exhaust pipe 30 is connected to the deodorization processing unit 29.

The deodorization processing unit 29 includes a deodorizing vessel 31 in which active sludge is contained, an air blowing pipe 32 for blowing air from the deodorizing communication pipe 28 into the active sludge and a pump 33. The air supplied onto the active sludge is exhausted to the atmosphere through the air exhaust pipe 30.

The processing apparatus having the two-staged processing vessel 1 has a feature that the size thereof can be further reduced without lowering a processing capacity as compared with the embodiment 1 provided with the single vessel. An example of waste processing actually carried out by charging kitchen garbage to the processing apparatus of the embodiment 2 will be specifically described in an embodiment 5.

Embodiment 3

Figure 6:
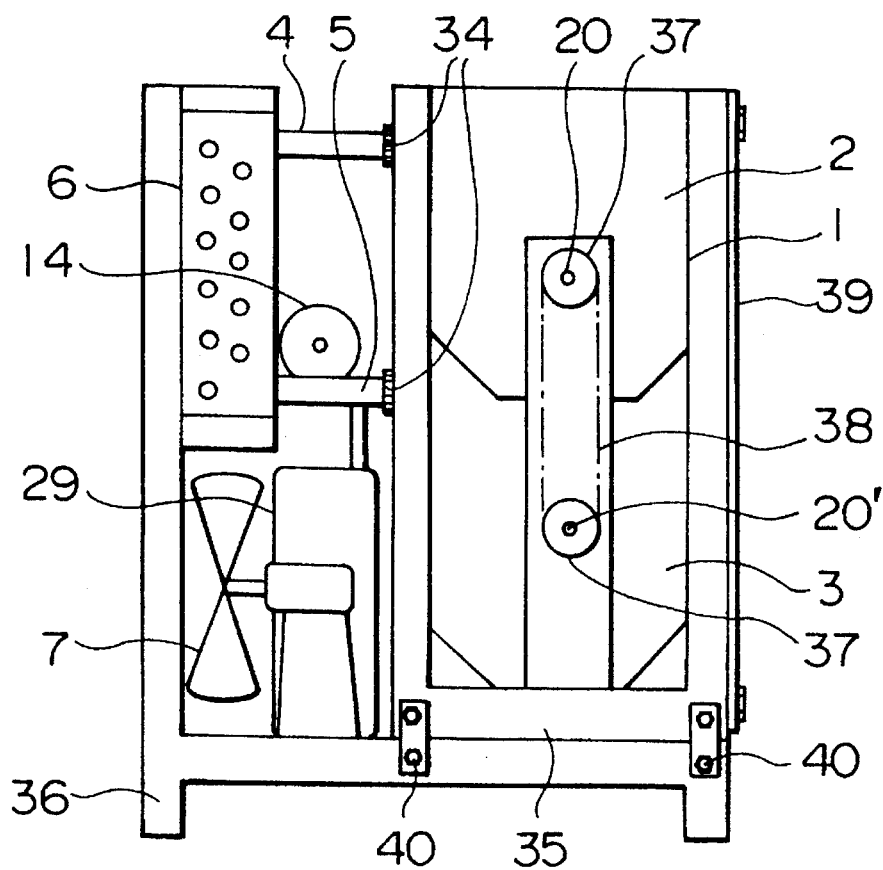
FIG. 6 is a side view of a still another embodiment of the solid organic waste processing apparatus of the present invention in the state that an outside box is removed.

FIG. 6 is a side view of a still another embodiment of the present invention in the state that an outside box is removed in the same way as FIG. 2 of the embodiment 2.

This apparatus has a feature such that a processing vessel 1 is supported by an independent auxiliary frame 35 and other components such as a heat exchanger 6 and the like are mounted on a main frame 36 so that the assembly of the components and the service and maintenance of the apparatus can be easily carried out.

An air intake pipe 4 and an air return pipe 5 are connected to the processing vessel 1 through a pipe connecting means 34 so that they can be removed from the processing vessel 1.

The processing vessel 1 is supported by the auxiliary frame 35 formed separatably from the main frame 36 by which the heat exchanger 6, an air supply means 7 and a deodorizing means 29 are supported.

Rotary shafts 20, 20' of the upper stage 2 and lower stage 3 of the processing vessel 1, bearings (not shown), a sprocket 37 and a chain 38 for connecting the upper and lower rotary shafts 20, 20' and an insulation member (not shown) are connected to the auxiliary frame 35, a part 39 of the outside box being also connected thereto.

Numeral 40 denotes a frame connecting means which is arranged such that the auxiliary frame 35 and the components connected thereto can be easily removed from the main frame when service, maintenance and the like are carried out.

Embodiment 4

Figure 7:
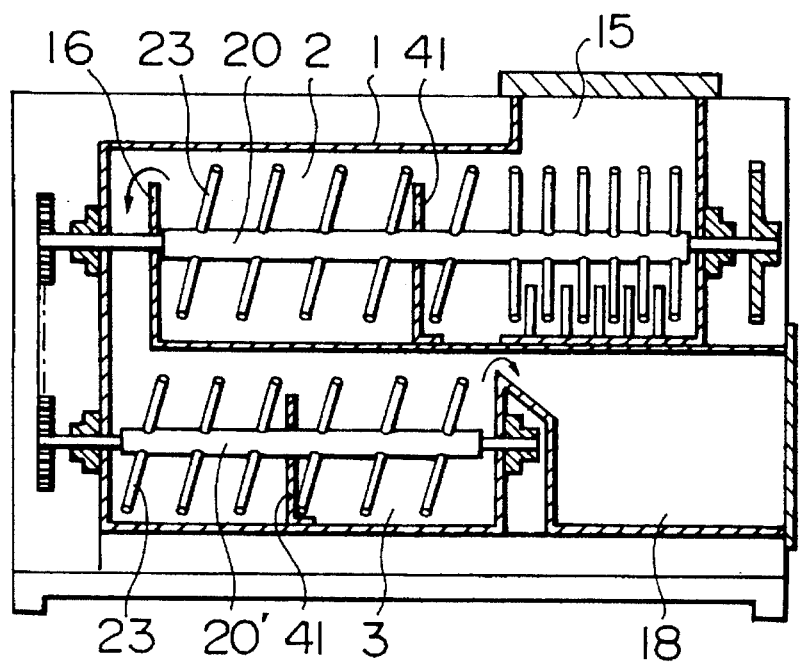
FIG. 7 is a front longitudinal cross sectional view of a processing vessel of a further embodiment of the solid organic waste processing apparatus of the present invention.

FIG. 7 is a front longitudinal cross sectional view of a processing vessel of a further embodiment of the processing apparatus of the present invention, wherein the processing vessel is obtained by improving the processing vessel 1 of the embodiment 2.

This apparatus has a feature such that an intermediate partition plate 41 is disposed in a processing unit and that agitation arms 23 in the processing unit are inclined with respect to rotary shafts 20, 20'. With this arrangement, an agitation width is more increased so that matters to be processed are prevented from staying on the bottom of the processing vessel and from sticking to the wall surface of the vessel by being baked.

More specifically, the rotary shaft 20, 20' are provided with the upper stage processing vessel 2 and lower stage processing vessel 3, respectively in the same way as the embodiment 2 and the plurality of agitation arms 23 are mounted on the rotary shafts 20, 20' with an inclining angle in the range of 3°–45° with respect to the radial direction of the rotary shaft.

As described above, with the inclination of the agitation arms 23 in the processing unit, when the rotary shafts 20, 20' rotate, an agitation width is increased in accordance with the degree of inclination of the agitation arms, so that the agitation arms can carry out an agitating motion in a range larger than that of vertical agitation arms and swing matters to be processed more effectively.

Further, an intermediate partition 41 is provided with the upper processing vessel 2 or lower processing vessel 3. Although each one intermediate partition is provided with these vessels, a plurality of intermediate partitions may be provided at predetermined intervals, when necessary. With this arrangement, when the waste in the processing vessel 1 becomes light in weight by the reduction of the water, the waste moves beyond the partition plate 41 to thereby falls into the adjacent vessel. Thus, by setting the intermediate partition plate to have a proper level of height, it becomes possbile to maintain the waste in the processing vessel 1 while the waste has a minimum water level necessary for the waste to be fermented, and to move the waste into the adjacent vessel beyound the partition plate 41 when the water contained in the waste is reduced to be less than the minimum water level, that is, it is possbile to make the intermediate partition plate have a function for automatically adjusting water. In this embodiment, by setting the partition plate 41 to have a height of 0.75×l to 1×l wherein l is the rotation diameter of the agitation arms 23, it becomes possbile to make the the intermediate partition plate 41 have a function for automatically adjusting water.

Although the agitation arms 23 in the upper and lower stages are inclined in the same direction in this embodiment, they need not always be inclined in the same direction but may be inclined in any direction so long as the range in which the agitation arms 23 are moved can be substantially increased.

Figure 16:
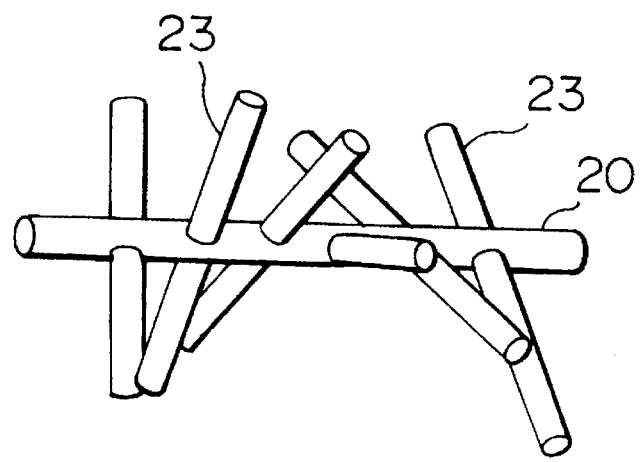
FIG. 16 is a perspective view showing the state that the positions where agitation arms are mounted on a rotary shaft are continuously dislocated circumferentially by a predetermined angle.

In any of the apparatuses of the embodiments 1–4, a rotating direction of the agitation arms 23, that is, a method of driving the rotary shaft 20 (20') can be selected from three rotation control sequences of, for example, (1) rotating the shaft continuously in a predetermined direction, (2) intermittently rotating the shaft with a predetermined stop period of time, and (3) rotating the shaft in a regular direction, stopping the shaft for a predetermined period of time and then rotating the shaft in another reverse direction, and the like. Further, as shown FIG. 16, when the agitation arms are mounted on the shaft in such a manner that the adjacent agitation arms 23 are continuously circumferentially dislocated each other (for example, at 30°), the matters to be processed can be easily moved in an axial direction. Since the driving method (3) was particularly excellent when an experiment was carried out by the use of kitchen garbage generated from restaurants, the process example shown in the following embodiment 5 was carried out in accordance with this method (3).

Embodiment 5

Solid organic waste composed of kitchen garbage generated from restaurants was processed by the apparatus of the embodiment 2 shown in FIGS. 2–5, and the kitchen garbage was composed of 50% of boiled rices, 10% of noodles, 20% of meat and fried food and 20% of vegetables and fruits on an average, and contained water of 70–75%. The waste was charged from the waste charge port 15 in an average amount of 16 kg a day and amounted to 325 kg in 20 days.

As environmental temperature conditions, an outside air temperature was 5°–15° C. and the inside of the processing vessel 1 was maintained to 55°–65° C. Further, the agitation arms 23 were rotated in a usual direction for 3 minutes, stopped for 3 minutes and then rotated in another reverse direction for 3 minutes by the drive means 22.

The processing vessel had an inside volume of 200 liters in the total of the upper and lower stages (the volume of the upper stage and that of the lower stage were divided to the ratio of 4:3). Prior to operation, total 50 kg of compost (aerobic bacteria) containing soil bacteria suitable for the temperature condition of about 60° C. was uniformly placed as the species of bacteria 17 on the bottom surface of the processing vessels of the upper stage and lower stage.

The average of 3 kg of compost was discharged a day during the test period and 58 kg of compost in total was discharged in 20 days.

As a result of the above experiment, the resulting volume of the kitchen garbage was reduced to about one sixth the original volume thereof, a component decomposition ratio was 30–40% and further discharged matters had a low water content of 15% or less. Thus, it was confirmed that the resulting compost could be handled easily because it did not become musty and had a low level of a bad odor.

Further, with respect to deodorization, the deodorizing vessel 31 was filled with active sludge conventionally used for water treatment in a water purification plant and a gas generated in the processing vessel 1 was supplied to the deodorizing vessel 31 and was deodorized under the same outside temperature condition during the same period, as the above. An amount of the gas to be supplied to the deodorizing vessel 31 was equal to the amount of air to be supplied (amount of fresh air to be taken in) to compensate the amount of oxygen consumed by fermentation. Further, it could be confirmed that a gas discharged into air had a very low level of a bad odor and a bad odor other than the odor intrinsic to the active sludge was not generated.

Embodiment 6

Figure 8:
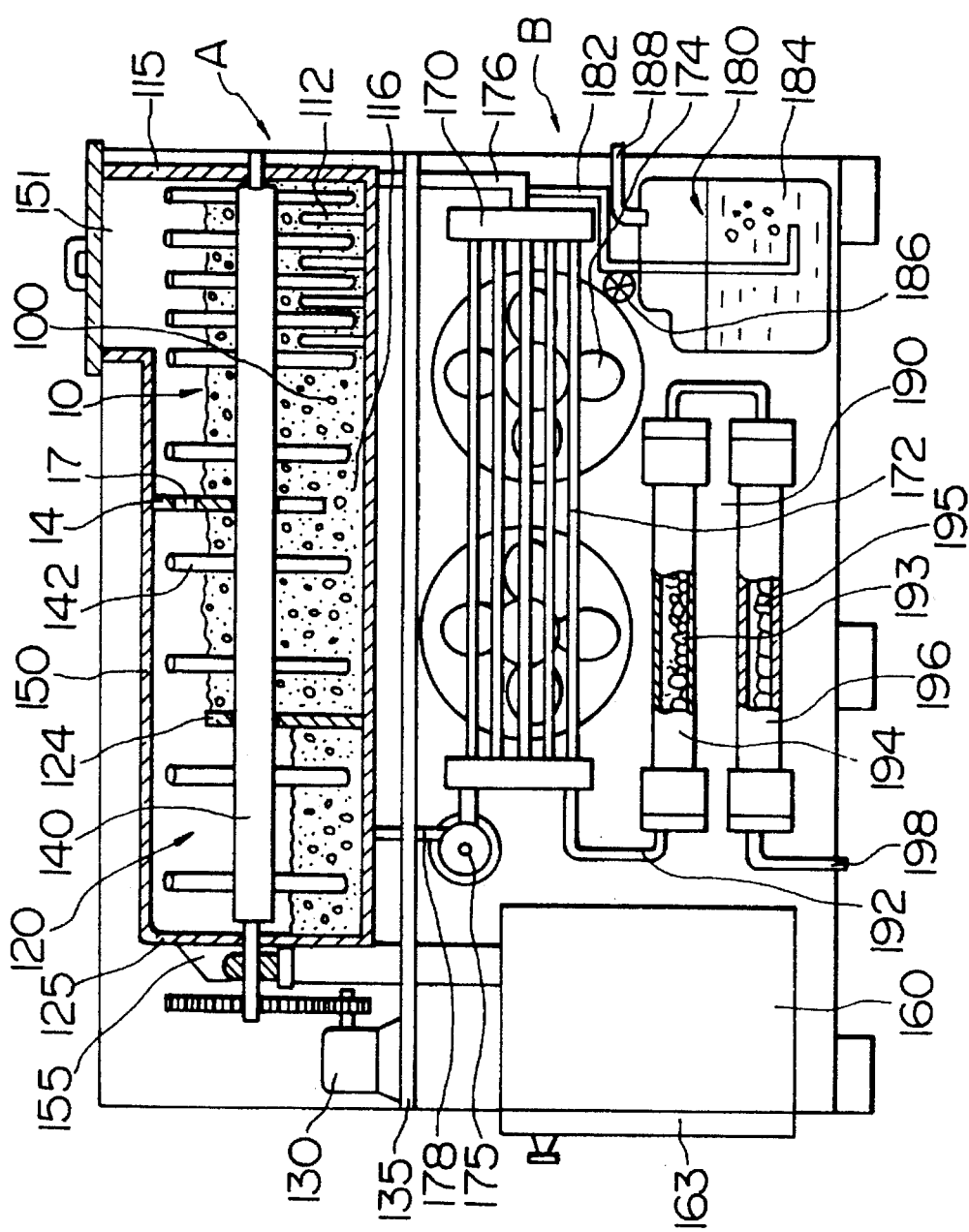
FIG. 8 is a front longitudinal cross sectional view of a further embodiment of the solid organic waste processing apparatus of the present invention.
Figure 9:
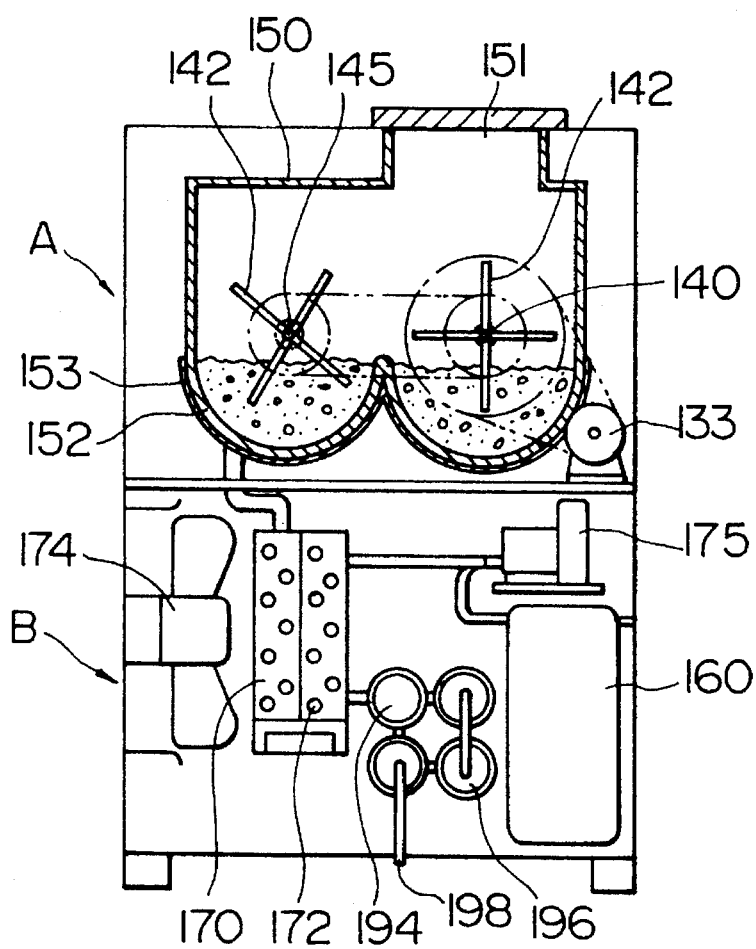
FIG. 9 is a side cross sectional view of the processing apparatus.
Figure 10:
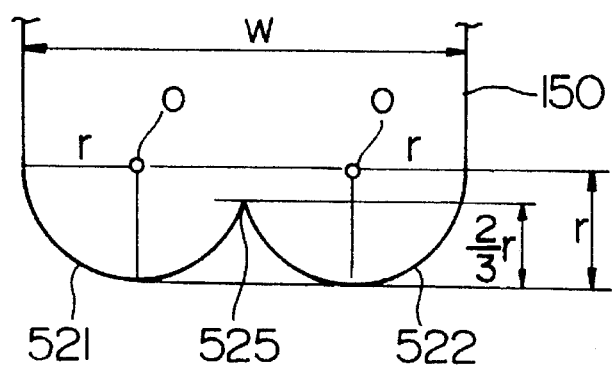
FIG. 10 is a diagram explaining a processing vessel used in FIG. 9.

FIG. 8 is a front vertical cross sectional view of the main part of an embodiment 6 of the processing apparatus of the present invention, and FIG. 9 is a side cross sectional view of the processing apparatus. In this embodiment, the solid organic waste processing apparatus includes a solid organic matter processing device A and a gas and liquid processing device B.

The solid organic matter processing device A includes a processing vessel 150 having a charge port 151 opened through the upper portion thereof. The processing vessel 150 has a box with a curved bottom surface 152 formed to the shape of substantially a Greek letter "ω" which has a cross section formed by connecting two semicircular arcs in parallel and the curved bottom surface 152 is divided into a first curved bottom surface 521 and a second curved bottom surface 522. Each of the first curved bottom surface 521 and second curved bottom surface 522 is formed to an arc having a center O and a radius r and a connecting point 525 where the first curved bottom surface 521 is connected to the second curved bottom surface 522 is located substantially at a height of ⅔ of "r" from the lower portion of the bottom surface.

A plurality of electric band-shaped heaters 153 as a means for heating the processing vessel 150 are attached around the outside wall of the curved bottom surface 152 formed to the Greek letter "ω" shape. The bottom portion of the processing vessel 150 is maintained to a temperature of 60° C.–80° C. by the heater 153 at which waste contained therein can be effectively and sufficiently fermented.

The processing vessel 150 includes a crushing unit 110 continuous to the charge port 151 and a processing unit 120 adjacent to the crushing unit 110.

The crushing unit 110 has comb-shaped arms 112 fixed therein, these arms being disposed on the side surface of the processing vessel 150, and is separated from the processing unit 120 by a charge side partition 114. The charge side partition 114 hangs down from the upper surface of the processing vessel 150 and a gap 116 is formed between the partition 114 and the lower surface of the processing vessel 150. Further, the size of the gap 116 can be adjusted by arranging the partition 114 in such a manner that it can slide in the height direction thereof. Further, the charge side partition 114 has a hole 117 defined on the upper portion thereof through which air is communicated between the crushing unit 110 and the processing unit 120.

The processing unit 120 is provided with an end plate side partition 124 at the center thereof which is fixed to the bottom of the vessel and a gap is formed between the upper portion of the partition 124 and the inside wall of the processing vessel 150. An end plate 125 is disposed to an end of the processing unit 120 and an end plate 115 is disposed to the side surface of the crushing unit 110, respectively so that the opposite ends of the processing vessel 150 of the solid organic matter processing device A are closed. An openable/closable lid is disposed to the waste charge port 151.

Two rotary shafts 140, 145 extending through the crushing unit 110 and processing unit 120 are disposed in the processing vessel 150 by being supported by both end plates 115, 125 thereof, an end of each of the rotary shafts 140, 145 being connected to a drive unit 130. The first rotary shaft 140 is located substantially at the center O of the curved bottom (semicircular shape) surface 521 and the second rotary shaft 145 is located substantially at the center O of the curved bottom surface 522. Agitation arms 142 are radially fixed to the rotary shafts 140, 145 at predetermined intervals. The agitation arms of the first rotary shaft 140 and the agitation arms of the second rotary shaft 145 are disposed so that they do not interfere one another or interfere with the fixed arms 112 in the crushing unit 110. A plurality of the agitation arms 142 are disposed in the crushing unit 110 and the processing unit 120, respectively. The first rotary shaft 140 is coupled with the second rotary shaft 145 outside the processing vessel 150 through a sprocket and chain or a gear and they are also coupled with the drive unit 130 having a motor 133.

A discharge port is defined to the end plate 125 of the processing unit 120 and a discharge tube 155 is connected through the discharge port. The discharge tube 155 has a cylindrical shape and the lower end thereof is opened toward a storing unit 160. The storing unit 160 is disposed at an end of the gas and liquid processing device B disposed below the solid organic matter processing device A, and matters (compost) processed in the processing vessel 150 drop into the storing unit 160 through the discharge tube 155 and are deposited therein.

The gas and liquid processing device B is disposed below the solid organic matter processing device A through a frame 135.

The gas and liquid processing device B includes a heat exchanging unit 170, a deodorization processing unit 180, a water purification unit 190 and the storing unit 160.

The storing unit 160 is provided with an openable/closable discharge gate 163 formed to the wall surface thereof to take out processed matters accommodated therein and the discharge gate 163 is arranged as a portion of the outside wall of the gas and liquid processing device B.

The heat exchanging unit 170 includes a heat exchanger 172 and a blower 174. The heat exchanger 172 has a plurality of air pipes disposed in parallel and interconnected to each other. The upstream side of the heat exchanger 172 is connected to a gas intake pipe 176 which is connected to the crushing unit 110 of the processing vessel 150, whereas the downstream end of the heat exchanger 172 is connected to the processing unit 120 through an air return pipe 178. A gas circulator 175 is disposed in the midway of the air return pipe 178 through which the heat exchanger 172 is connected to the processing unit 120. The gas circulator 175 serves to supply air in the direction of the processing unit 120. When the gas circulator 175 is operated, the gas in the vessel is taken into the air pipes of the heat exchanger 172 from the crushing unit 110 side through the gas intake pipe 176 and positively supplied and circulated to the processing unit 120 through the air return pipe 178. During this period, air containing vapor due to fermentation which is supplied from the crushing unit 110 and passes through the air pipes is cooled by outside air of low temperature blown thereto by the blower 174 disposed in the path of the air so that water (moisture) contained in the vapor is changed to water droplets. Then, the air from which water is removed is returned to the processing unit 120 through the air return pipe 178.

A deodorizing communication pipe 182 branched from the gas intake pipe 176 is disposed to a portion of the path through which gas is circulated from the gas circulator 178 and connected to the deodorization processing unit 180.

The deodorization processing unit 180 includes a deodorizing vessel 184, a deodorizing blower 186 disposed in the path of the deodorizing vessel communication pipe 182, and an exhaust pipe 188 having an end opened through the upper portion of the deodorizing vessel 184 and the other end opened to the outside air. The deodorizing unit 184 is filled with liquid containing microorganisms for decomposing an odor. When the deodorizing blower 186 of the deodorizing unit 180 is operated, a gas containing an odor is introduced from the deodorizing communication pipe 182 into the deodorizing vessel 184 and aerated in the liquid so that the gas comes into contact with the microorganisms and so that the odor component in the gas is decomposed, then odorless air being exhausted to the outside of the apparatus through the exhaust pipe 188.

An amount of the air subjected to the deodorizing process and exhausted to the outside, that is, an amount of air transferred by the blower 186 is made to substantially correspond to the air consumed in the processing vessel 150 by fermentation, and this air is supplied through the clearance between the processing vessel 150 and the charge port 151, the clearance between the storing unit 160 and the discharge gate 163, and the like.

The liquid purification unit 190 includes a drain pipe 192 disposed downward of the heat exchange unit 170 to discharge water produced from vapor condensed by exchanging the heat thereof, an adjustment tank 194 and a processing tank 196 are connected to the drain pipe 192, the adjustment tank 194 being filled with a weak alkaline material 193 (limestone, lime) and a processing tank 196 being filled with a carrier 195 to which microorganisms are fixed, and further a water discharge pipe 198 opened to the outside of the apparatus is disposed behind the processing tank 196. The carrier 195 to which the microorganisms (bacteria) are fixed is composed of polyvinyl alcohol (PVA) formed to a body having a number of honeycomb-shaped holes in which aquatic bacteria are contained. Since a reaction caused by the fermentation in the processing unit 120 is accompanied with weak acid such as fatty acid, acetic acid etc., water changed to water droplets by the heat exchange unit 170 exhibits weak acidity. This acid water is neutralized by the weak alkaline material 193 filled in the adjustment tank 194. Further, although some organic matters float in the water made to droplets, they are decomposed in the processing tank 196 disposed downward of adjustment tank 194 and filled with the carrier 195 to which the microorganisms are fixed and thus liquid which is neutralized and from which the organic materials are removed is discharged from the discharge pipe 198.

Each of the adjustment tank 194 and processing tank 196 of the liquid purification unit 190 disposed in the gas and liquid processing device B is formed to have a shape of a pipe at least one end of which can be opened and closed in order not to lower the space efficiency of the respective components disposed in the gas and liquid processing device B. With the openable/closable arrangement of the one end of the tanks or the pipes, the pipes can be easily filled with the weak alkaline material 193 and carrier 195 to which the microorganisms are fixed and further since these tanks are made of the pipes, they can be also effectively mounted to the apparatus from a view point of mounting space.

Next, an operation mechanism of the solid organic waste processing apparatus will be described. Species of bacteria 100 for fermentation are previously put on the curved bottom portion 152 of the processing vessel 150. The species of bacteria are, for example, species of aerobic bacteria and the like collected from compost, and the like. First, the drive unit 130 is driven to rotate the rotary shafts 20, 20' and kitchen garbage as a matters to be processed is charged from the charge port 151. Solid matters are crushed between the fixed arms 112 and the agitation arms 142 in the crushing unit 110 and oxygen is supplied into the kitchen garbage scooped up by the agitation arms 142. At this time, since the connecting portion 525 where the first curved bottom surface 521 is connected to the second curved bottom surface 522 has the height of ⅔ of r and the agitation arms 142 pass through the connecting portion 252 in an inclined state, the matters agitated by the agitation arms 142 are free to move between the first curved bottom surface 521 and the second curved bottom surface 522 and thus the agitation, mixing and crushing of the matters are promoted. The matters to be processed made to a mud state sequentially flow into the processing unit 120 through the gap 116 below the partition 114.

In the processing unit 120, the crushed organic matters to be processed are further agitated by the agitation arms 142 and uniformly mixed with the specimens of bacteria 100. Aerobic bacteria ferment and decompose the matters to be processed. At this time, the heater 153 disposed around the outside surface of the bottom portion is controlled by the thermostat (not shown) so that it is maintained at a suitable temperature of 50°–80° C. to thereby assist the promotion of the fermentation and decomposition of the matters to be processed in the processing vessel 150. Since the specimens of bacteria proliferate by themselves by eating organic waste, they are needed only when the operation of the apparatus starts for the first time and need not be supplemented while the apparatus is in operation because aerobic bacteria always exist and serve as specimens of bacteria to be charged next time.

In addition, when next kitchen garbage is charged from the charge port 151, it overflows and overflown garbage flows into the next region though the gap above the charge side partition 114 and the gap below the end plate side partition 124. The water (moisture) contained in the matters to be processed which have moved downward of the processing vessel 150 is evaporated and the matters are made to powder compost. When a predetermined amount of the processed matters (compost) are stored in the processing vessel 150, the compost drops into the storing unit 160 from the end plate 125 and recovered from the discharge gate 163.

A gas containing water generated in the processing vessel 150 when the garbage ferments is processed by the gas and liquid processing device B. The gas of high temperature and high humidity (mainly composed of air accompanied with a bad odor and vapor) is taken into the high temperature side (upstream side) of the heat exchanger 172 from the crushing unit 110 through the gas intake pipe 176 by the operation of the gas circulator and flows through the air pipes. While passing through the heat exchanger 172, the vapor in the gas is condensed to water by exchanging the heat thereof with air supplied by the blower 174 and the water is discharged from the low temperature side (downward side) of the heat exchanger 172 through the drain pipe 192. On the other side, the air from which the water is removed is returned into the processing vessel 150 through the air return pipe 178 and absorbs again the water (moisture) in the processing vessel 150. Water dropped from the drain pipe 192 is supplied to the adjustment tank 194 and neutralized by the weak alkaline material (limestone, lime) and further the organic matter contained in the water is decomposed by the microorganisms 195 in the processing tank 196. Thus, the water is made harmless and discharged from the discharge pipe 198 to the outside of the apparatus.

Further, a gas flowing downward through the gas intake pipe 176 of the gas circulation path is partly supplied to the deodorizing communication pipe 182 branched from the pipe 176. The gas is blown into the deodorizing vessel and the bad odor of the gas is decomposed by coming into contact with the microorganisms in the vessel and exhausted from the exhaust pipe 188 to the outside of the apparatus as odorless air. Since the pressure of air in the processing vessel 150 is reduced in proportion to an amount of the exhausted air, air is supplied through the clearance between the processing vessel 150 and the charge gate of the charge port 151, the clarence between the storing unit 160 and the discharge gate 163 and the like. Therefore, the inside of the circulation system of the apparatus is maintained substantially near to the atmospheric pressure as a whole.

Since the connecting portion 525 where the first curved bottom surface 521 of the processing vessel 150 is connected to the second curved bottom portion 522 thereof is located below the rotary shafts, the size W of the processing vessel 150 in the direction perpendicular to the rotary shafts can be reduced. Thus, the apparatus can be made small in size as a whole. Further, since a large amount of waste can be simultaneously agitated and mixed by the two rotary shafts 140, 15, a processing efficiency can be improved with an increased processing speed.

Since this apparatus is arranged to have a relatively small size and since waste can be continuously charged to the apparatus, the apparatus can be easily operated and maintained. When it is applied to the industrial fields where kitchen garbage is generated, the apparatus can process waste without depending upon waste collectors and thus the waste can be economically processed. Further, since a gas and liquid discharged to the outside of the apparatus are harmless and odorless, surroundings are not adversely affected by them.

Since the species of bacteria 100 prepared first proliferate by themselves by eating kitchen garbage (solid organic waste), they are needed only when the operation of the apparatus starts for the first time and need not be supplemented while the apparatus is in operation because the aerobic bacteria always exist and serve as specimens of bacteria to be charged next time.

Further, since water generated when solid organic waste ferments is removed by the heat exchanger 170 and since condensed water is purified and discharged to the outside of the apparatus, recovered compost is dry and almost odorless powder even if a conventionally used water content adjustment material such as sawdust, rice hulls and the like is not charged to absorb water. Therefore, the compost can be recovered as manure with a very high added value for raising farm products, garden plants and other general plants and this apparatus is preferable from the view point of the reuse of waste.

Embodiment 7

Figure 11:
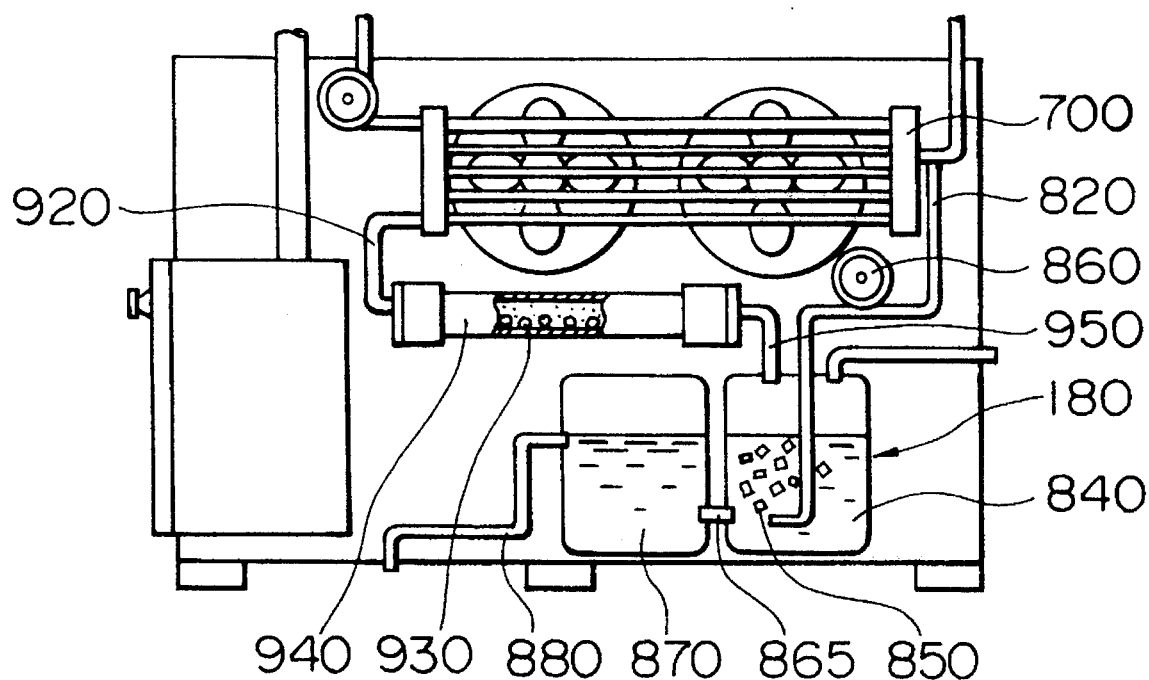
FIG. 11 is a front longitudinal cross sectional view of a gas and liquid processing unit used in the solid organic waste processing apparatus of the present invention.

This embodiment is arranged such that the deodorization processing mechanism of a gas and liquid processing device B also serves to remove an organic matter contained in water to be discharged. The arrangement of this embodiment will be described with reference to a cross sectional view of the main part of the gas and liquid processing device of this embodiment shown in FIG. 11.

Since a solid organic waste processing device is the same as that described with reference to the embodiment 6, the description thereof is omitted.

The gas and liquid processing device is provided with a heat exchange unit 700 similar to that of the embodiment 6. An adjustment tank 940 is connected to a drain pipe 920 located downward of the heat exchange unit 700. The adjustment tank 940 is filled with a weak alkaline material 980 (limestone, lime). A deodorization processing unit 180 has a deodorizing communication pipe 820 branched from a part of a gas circulation path and the deodorizing communication pipe 820 is opened in the lower portion of a deodorizing vessel 840. The deodorizing vessel 840 is filled with a carrier 850 to which microorganisms are fixed, the carrier being similar to that used in the embodiment 6, and an odor is decomposed by the microorganisms.

Further, a water level tank 870 is disposed in the vicinity of the deodorizing vessel 840 which is communicated with the water level tank 870 through a coupling pipe 855 disposed at the lower portion thereof. Further, a water discharge pipe 880 is attached to the water level tank 870 at the position thereof which is as high as the water level in the deodorizing vessel 840 and opened to the outside of the apparatus. Since the water discharge pipe 880 of the water level tank 870 is located at the water level of the deodorizing vessel 840, the water level in the deodorizing vessel 870 is not changed so that the carrier 850 is in good contact with a gas to be aerated which is supplied from the deodorizing communication pipe 820 at all times.

A dropping pipe 950 coupled with the adjustment tank 940 is opened through the upper portion of the deodorizing vessel 840 to drop water passing through the adjustment tank 940 into the deodorizing vessel 840. The organic matter in the water flowing into the deodorizing vessel 840 is decomposed and removed by the microorganisms of the carrier 850.

The gas and liquid processing device arranged as described above takes a gas containing vapor into the pipe of the heat exchanger 700, cools the gas by outside air blown thereto and changes the water contained in the gas to droplets while returning the air from which water is removed into the solid organic matter processing device. The water produced by condensing the vapor by exchanging the heat thereof is supplied to the adjustment tank 940 filled with the weak alkaline material 930 (limestone, lime) through the drain pipe 920, neutralized by the weak alkaline material 930 and stored in the deodorizing tank 840 through the dropping pipe 950. Further, a gas containing an odor and supplied from the deodorizing communication pipe 820 by a deodorizing blower 860 comes into contact with the carrier 850 which has the microorganisms fixed thereto and which is filled in the deodorizing vessel 840, by being aerated in the liquid of the deodorizing tank 840. As a result, the odor component of the gas is decomposed and the gas is made to odorless air and at the same time some organic matters contained in the water discharged through the adjustment tank 940 are decomposed by the carrier 850 which has the microorganisms fixed thereto and which is filled in the deodorizing vessel 840. Then, the water in the deodorizing vessel 840 is transferred to the level adjustment tank 870 by an amount corresponding to the water supplied into the deodorizing vessel 840 and the water overflowing the position where the water discharge pipe 880 is attached to the water level tank 870 is discharged to the outside of the apparatus.

As described above, since the solid organic waste processing apparatus shown in this embodiment can deodorize a gas while decomposing the organic matters contained in water to be discharged by the deodorizing processing means (deodorizing vessel) 840 at the same time, the arrangement of the apparatus can be simplified, and thus a gas can be deodorized and liquid can be purified by a small apparatus.

Embodiment 8

Figure 12:
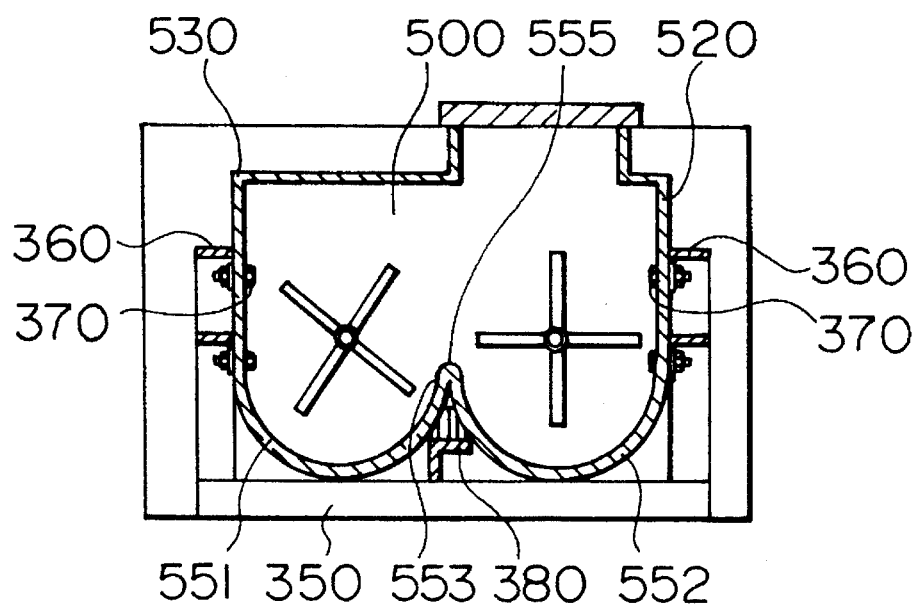
FIG. 12 is a side view of the main part showing the arrangement of a processing unit of the solid organic waste processing apparatus of the present invention.

This embodiment shows a solid organic waste processing apparatus by which the processing vessel of a solid organic matter processing unit A is more strongly disposed. The arrangement of the processing vessel will be described with reference to a cross sectional view of the main part of the solid organic matter processing unit A shown in FIG. 12.

The processing vessel 500 has opposite side walls 520, 530 which are fixed through bolts 370 to side angle steels 360 secured to the frame 350 of the solid organic waste processing apparatus. Further, the portion where a first curved bottom surface 551 is combined with a second curved bottom surface 552 is supported by a bottom angle steel 380 secured to the frame 350, the above combining portion being located below the connecting portion 555 where the first portion 551 is connected to the second portion 552. The bottom angle steel 380 is secured to the curved bottom surfaces 551, 552 through bolts.

These side angle steels 360 and bottom angle steels 380 support the weight of the processing vessel 500 as a whole and prevent force from concentrating onto the first curved bottom surface 551 and second curved bottom portion 552 so that the cross sectional structures thereof are not deformed and so that the agitation arms fixed to two rotary shafts are prevented from coming into contact one another by the deformation of the semicircular inside wall of the vessels having the first and second curved bottom surfaces 551 and 552. The same effect can be obtained even if the processing vessel is supported by channel steels in place of the angle steels.

Embodiment 9

Figure 13:
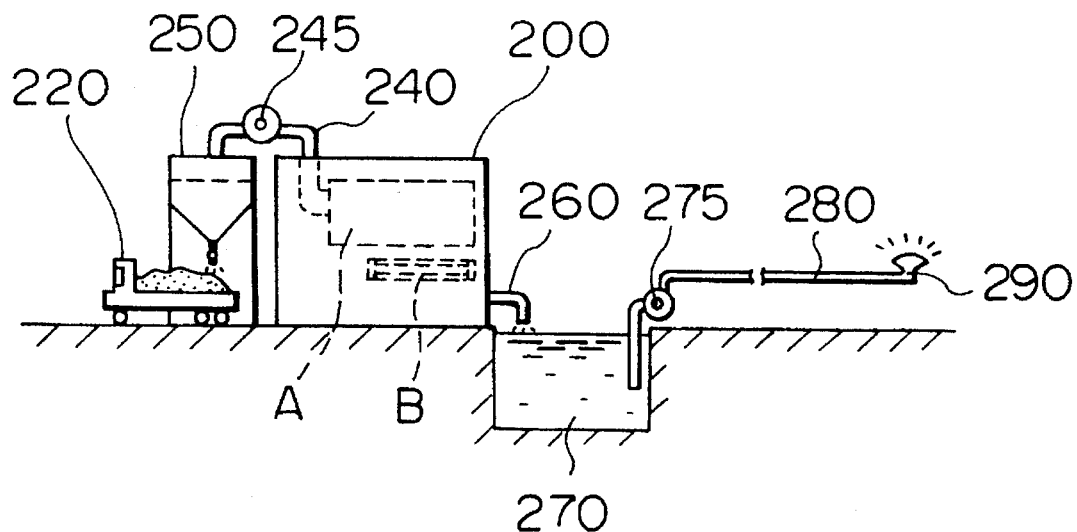
FIG. 13 is a schematic diagram showing a further embodiment of the solid organic waste processing apparatus of the present invention.

This embodiment shows a solid organic waste processing apparatus which is suitably installed to regions having a less amount of rain or having insufficient water, deserts, and the like. FIG. 13 is a diagram explaining an arrangement of the processing unit of the solid organic waste processing apparatus of this embodiment, wherein the solid organic waste processing apparatus 200 is arranged separately from a compost storing apparatus 250.

A solid organic matter processing device A and a gas and liquid processing device B which have the same arrangement as those of the embodiment 1 are disposed in the solid organic waste processing apparatus 200.

The compost storing apparatus 250 in which compost is deposited and stored is disposed adjacent to the solid organic waste processing apparatus 200. The solid organic matter processing device A of the solid organic waste processing apparatus 200 is connected to the compost storing apparatus 250 through a compost discharge pipe 240, and a blower 245 is disposed in the transfer path of the compost discharge pipe 240 to promote the transfer of the compost.

Further, a water storage tank 270 is disposed adjacent to the solid organic waste processing apparatus 200 and a discharge pipe 260 is opened toward the water storage tank 270 so that water from the gas and liquid processing device B of the solid organic waste processing apparatus 200 is supplied dropwise to the tank 270. Further, a water supply pipe 280 connected to an irrigation unit 290 having a sprinkling mechanism is connected to the water storage tank 270 through a pump 275.

With this arrangement, compost discharged from the solid organic matter processing device A of the solid organic waste processing apparatus 200 is discharged into the compost storing apparatus 250 through the compost discharge pipe 240. The compost deposited in the compost storing apparatus 250 is transported by a truck 220 and spread over farms requiring manure.

Water discharged from the gas and liquid processing device B is stored in the water storage tank 270 through the discharge pipe 260. Then, water pumped up by the pump 275 is sprinkled by the irrigation unit 290 through the water supply pipe 280 to the surroundings to irrigate dry soil in the surroundings.

When solid organic waste (kitchen garbage) is directly spread over wasteland or sandy land, since it generates heat by being rotten and fermented in soil and further takes oxygen from the roots of plants, the plants are made to a so-called root-rotted state and become difficult to be raised. When the solid organic waste processing apparatus 200 is combined with the irrigation unit 290 and the like and compost which is dried and made to powder is spread over wasteland, however, the wasteland can be made rich as well as when water, which is said to be contained in kitchen garbage in an amount of 80 wt %, is purified to an odorless and harmless state and sprinkled to dry land, the wasteland and sandy land can be planted with trees, whereby nature can be prevented from being destroyed by dumped kitchen garbage and environmental safeguards and planting of trees can be promoted.

Embodiment 10

Figure 14:
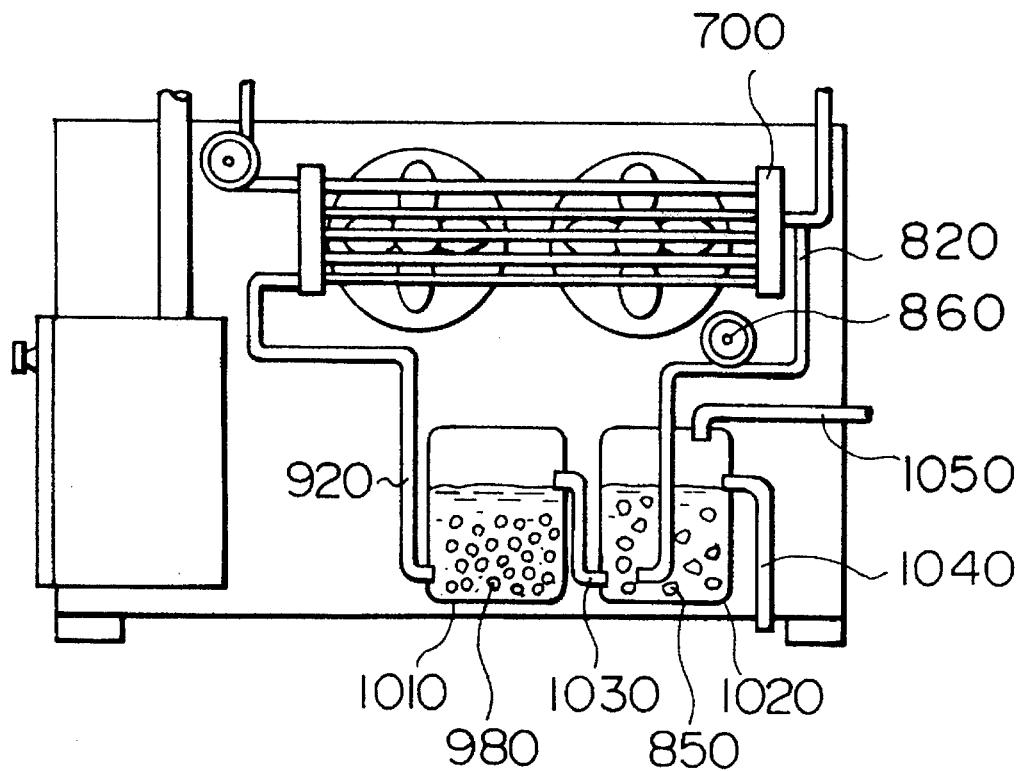
FIG. 14 is a front schematic view showing a further embodiment of the solid organic waste processing apparatus of the present invention.

A feature of an embodiment 10 shown in FIG. 14 is that the function of the water level tank 870 and the function of the adjustment tank 940 in the embodiment 7 (FIG. 11) is carried out by a single adjustment tank 1010. Since the other arrangement of the embodiment 10 is the same as that of the embodiment 7, only the arrangement relating to the adjustment tank 1010 will be described.

The adjustment tank 1010 is connected to a drain pipe 920 and filled with a weak alkaline material 980 (limestone etc.). An end of the drain pipe 920 is connected to the bottom of the adjustment tank 1010 to introduce water generated in a heat exchanger into the adjustment tank 1010. A deodorizing vessel 1020 (in which a carrier 850 containing microorganisms is accommodated in the same way as the embodiment 7) is disposed adjacent to the adjustment tank 1010 and the upper portion of the adjustment tank 1010 is connected to the bottom portion of the deodorizing vessel 1020 through a communication pipe 1030 so that water supplied from the adjustment tank 1010 to the deodorizing vessel 1020 is purified by the microorganisms in the deodorizing vessel 1020. A water discharge pipe is attached to the upper portion of deodorizing vessel 1020 to discharge the purified water exceeding a predetermined amount. An end of a deodorizing communication pipe 820 having the same function as that of the embodiment 7 is disposed to the bottom of the deodorizing vessel 1020 and an exhaust pipe 1050 is attached to the upper portion of the deodorizing vessel 1020 so that a gas supplied from the deodorizing communication pipe 820 into the deodorizing vessel 1020 and deodorized therein is exhausted through the exhaust pipe 1050.

Operation of this embodiment 10 will be described below. Water generated in the heat exchanger and containing an organic matter is supplied into the adjustment tank 1010 and neutralized by the weak alkaline material 980 (limestone etc.) and the neutralized water is introduced to the bottom of the deodorizing vessel 1020 through the communication pipe 1030 and discharged from the discharge pipe 1040 with the organic material thereof removed in the deodorizing vessel 1020 by the action of the microorganisms contained therein. Further, a gas containing a bad odor and supplied from the deodorizing communication pipe 820 is also deodorized by the action of the microorganisms in the deodorizing vessel 1020 and exhausted from the exhaust pipe 1050.

Embodiment 11

Figure 15:
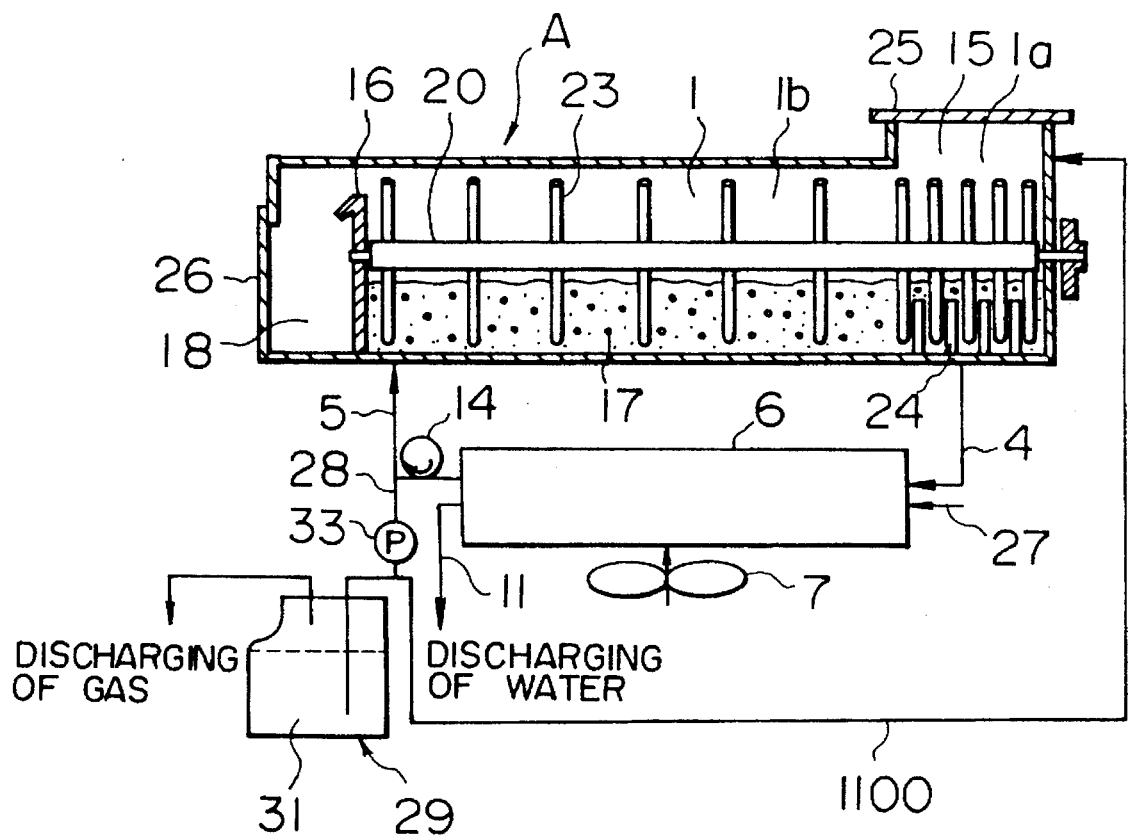
FIG. 15 is a schematic view showing a further embodiment of the solid organic waste processing apparatus of the present invention.

An embodiment 11 shown in FIG. 15 is arranged such that one end of a separate air return pipe 1100 is connected to the pipe disposed downward of the pump 33 with another end of the pipe 1100 being opened to the crushing unit 1a having the same structure as in the embodiment 1 so that a part of air exhausted by the pump 33 is supplied to the crushing unit 1a through the air return pipe 1100 to thereby promote dehydration in the crushing unit 1a. The other arrangement of the embodiment 11 is the same as that of the embodiment 1.

As described above, expected objects can be achieved by the present invention. More specifically, there can be provided the solid organic waste processing apparatus which does not scatter a bad odor and a lot of vapor to the surroundings, does not need the addition of sawdust, rice hulls etc. as a water content adjustment material and is capable of being charged with kitchen garbage at any time and capable of decomposing the garbage at a high decomposing ratio at a high speed.

Further, there can be provided the small solid organic waste processing apparatus which can be installed in a very small space when installed in the kitchen and the like of restaurants. Furthermore, since recovered compost can be effectively utilized as manure for growing plants and since kitchen garbage can be recovered and reused as a matter having a value, the present invention can greatly contribute to industries from the view point of environmental safeguards. Further, in the present invention, both of the heat exchanger and the circulation constitution comprising the air-taking-out pipe and the air-return pipe act to realize at the same time both respects, which apparently contradict each other, that the water is removed for reducing the weight of matter to be processed and that the moisture in the processing vessel is maintained in such a necessary level as the sufficient fermentation can occur by the action of the aerobic bacteria, with the result that the apparatus of the present invention brings about a condition appropriate for the aerobic becteria to act for the sufficient fermentation of the waste.

This apparatus has the simplified driving mechanism, and since bacteria for assisting fermentation proliferate by themselves by eating an organic matter while the apparatus is in operation, specimens of bacteria only need be supplied at the start of the apparatus for the first time and they need not be supplemented. Thus, the apparatus can be easily operated and maintained. When this apparatus is applied to industrial fields such as food processing industry, food service industry and the like where kitchen garbage is generated at all times, the apparatus can process waste without depending upon waste collectors and thus the waste can be economically processed. Further, since a gas and liquid discharged to the outside of the apparatus is harmless and odorless and surroundings are not adversely affected by them, the apparatus may be installed in the vicinity of the location where waste is generated and the waste can be dumped by being made to compost and water.

Further, since water generated when solid organic waste is fermented is removed by the heat exchanger, purified and discharged to the outside of the apparatus, even if a conventionally used water content adjustment material such as sawdust, rice hulls etc, is not charged to absorb water, compost is almost odorless dry powder with a very high added value and can be recovered as manure for growing farm products, garden plants, other general plants and this apparatus is preferable from the view point of the reuse of waste. Further, since dry air from which water is removed is returned to the processing vessel, matters to be processed are quickly dried.

Further, when kitchen garbage is directly dumped into the ground, the growing of plants is apt to be destroyed due to the heat generated when an organic matter ferments and due to the consumption of oxygen needed by the fermentation thereof, that is there is such a fear that nature is destroyed. However, the combination of the apparatus by which dry compost and pollution-free water can be created, the sprinkling means and the compost storing means contributes to plant arid regions, poor ground and the like with trees.

What is claimed is:

1. An apparatus for processing solid organic waste by crushing and/or agitating and fermenting the waste, characterized by comprising:

a solid organic matter processing device including a processing vessel provided with a crushing unit for receiving and crushing the solid organic waste and a processing unit for agitating and fermenting the crushed waste;

a heat exchanger disposed outside said solid organic matter processing device which heat exchanger condenses vapor in a gas supplied from the processing vessel of said solid organic matter processing device to thereby change the vapor to liquid and to discharge the liquid; and gas circulation means for providing a gas circulation path through which the inside of the processing vessel of said solid organic matter processing device is operably connected to said heat exchanger and through which a gas in the processing vessel of said solid organic matter processing device is supplied into said heat exchanger, almost all of the gas processed in said heat exchanger being returned to said solid organic matter processing device while a portion of the gas processed in said heat exchanger or a portion of the gas supplied from the processing vessel of said solid organic matter processing device is discharged to the outside of the apparatus.

2. An apparatus for processing solid organic waste by crushing and/or agitating and fermenting the waste according to claim 1, characterized by further including a deodorization processing unit for deodorizing at least a portion of a gas supplied from said processing vessel which deodorization processing unit discharges the deodorized gas to the outside and/or deodorizes at least a portion of a gas processed by said heat exchanger and then discharges the deodorized gas to the outside of the apparatus.

3. An apparatus for processing solid organic waste by crushing and/or agitating and fermenting the waste according to claim 2, characterized by further including a liquid purification unit for neutralizing water in said heat exchanger, neutralized water produced in said liquid purification unit being supplied to said deodorization processing unit where the organic matter in the neutralized water is removed while the neutralized water is used to maintain the water in said deodorization processing unit to a predetermined level and while excessive water from which the organic matter is removed is discharged.

4. An apparatus for processing solid organic waste by crushing and/or agitating and fermenting the waste according to any one of claim 1 to claim 3, characterized in that a portion of the gas processed in said heat exchanger is supplied to said crushing unit or to the vicinity of said crushing unit.

5. An apparatus for processing solid organic waste by crushing and/or agitating and fermenting the waste according to claim 1 or claim 2, characterized in that said crushing unit has a charge port for charging the solid organic waste, said processing unit has a heating unit by which said processing unit is kept to a predetermined processing temperature at which the crushed matters to be processed are agitated under the existence of species of aerobic bacteria and sufficiently fermented, said gas circulation means carries out a gas circulation so that a gas containing vapor in said processing vessel is supplied from the crushing unit side thereof to said heat exchanger and the gas processed by said heat exchanger is returned to the processing unit of said processing vessel, said heat exchanger has an air intake port at the high temperature side thereof for taking air from the outside in an amount corresponding to the air consumed by a fermentation process executed by the aerobic bacteria in said processing unit, said deodorization processing unit has a deodorizing communication pipe branched from a path through which an heat-exchanged gas is returned from the low temperature side of said heat exchanger to said processing vessel so that a gas corresponding to an amount of the air taken through said air intake port is deodorized and exhausted to the outside through a deodorizing vessel, and said processing vessel further has a storing unit for recovering matters processed by said processing vessel.

6. An apparatus for processing solid organic waste by crushing and/or agitating and fermenting the waste according to claim 1, characterized in that a drain pipe is disposed to a path for returning the heat-exchanged gas to said processing vessel to thereby discharge water produced from the vapor condensed during exchanging of the heat thereof.

7. An apparatus for processing solid organic waste by crushing and/or agitating and fermenting the waste according to claim 1 or claim 2, characterized in that comb-shaped fixed arms are disposed on the bottom of said processing vessel in the crushing unit thereof and agitation arms are mounted on a rotary shaft in said crushing unit and said processing unit, respectively and each of said agitation arms located in said crushing unit passes between adjacent ones of said fixed arms in such a manner that it is about to be in contact therewith to thereby crush the solid organic waste.

8. An apparatus for processing solid organic waste by crushing and/or agitating and fermenting the waste according to claim 1 or claim 2, characterized in that a circulation fan is disposed to the path through which a heat-exchanged gas is returned to said processing vessel to thereby circulate the gas to said processing vessel, and that means for introducing outside air is provided which supplies the same into said heat exchanger.

9. An apparatus for processing solid organic waste by crushing and/or agitating and fermenting the waste according to claim 6, characterized in that the extreme ends of at least a pair of said adjacent agitation arms are connected by a coupling member, and that said coupling member promotes agitation in said processing vessel and prevents the solid organic waste from adhering to said processing vessel.

10. An apparatus for processing solid organic waste by crushing and/or agitating and fermenting the waste according to claim 1, characterized in that a circumferential angle of each of the agitation arms mounted on a rotary shaft is continuously dislocated circumferentially by a predetermined angle so that the solid organic waste is axially moved toward the direction in which the waste is left from said crushing unit.

11. An apparatus for processing solid organic waste by crushing and/or agitating and fermenting the waste according to claim 1, characterized in that said processing vessel is subdivided into multi-staged vessels disposed vertically with an upper processing vessel including a crushing unit having a charge port and with another lower processing vessel being provided with a processing unit, and that processed matters sequentially overflow the end plates of said respective processing vessels.

12. An apparatus for processing solid organic waste by crushing and/or agitating and fermenting the waste according to claim 1, characterized in that intermediate partitions are disposed at least in the processing units of said processing vessels to separate the inside of said processing vessels to thereby provide a plurality of vessel portions having dam effect for the matters to be processed.

13. An apparatus for processing solid organic waste by crushing and/or agitating and fermenting the waste according to claim 1, wherein said processing vessel has a rotary shaft extending therethrough and said crushing unit has agitation arms formed to a bar-shape.

14. An apparatus for processing solid organic waste by crushing and/or agitating and fermenting the waste according to claim 1, wherein said processing unit has a rotary shaft extending therethrough, agitation arms being secured to the rotary shaft and being inclined with respect to said rotary shaft by a predetermined angle and being formed to a bar-shape.

15. An apparatus for processing solid organic waste by crushing and/or agitating and fermenting the waste according to claim 1, wherein said processing vessel has a rotary shaft extending therethrough and the apparatus further comprises a drive mechanism connected to said rotary shaft to rotate the agitation arms in said processing vessel and said rotary shaft is made to rotate in sequence in a usual direction, to stop and to rotate in a reverse direction for a predetermined period of time, respectively.

16. An apparatus for processing solid organic waste by crushing and/or agitating and fermenting the waste according to claim 1, characterized in that said processing vessel has an upper box-shaped processing vessel, a lower box-shaped processing vessel disposed in two stages, an air intake pipe for taking air from said upper stage processing vessel, and an air return pipe for returning air to said lower stage processing vessel, both of said pipes being disposed outside of said processing vessels, said heat exchanger being connected to said air intake pipe and said air return pipe, air supply means being provided to supply outside air to said heat exchanger, that said heat exchanger is provided with a vertically disposed tubular inlet pipe connected to said air intake pipe, a vertically disposed tubular outlet pipe connected to said air return pipe, and a plurality of heat exchange pipes connected to said inlet pipe and said outlet pipe and extending substantially in a horizontal direction, that a drain pipe is disposed below said outlet pipe, that said processing vessel has heating means and temperature keeping means so that the inside of said processing vessel is kept to a predetermined temperature at which aerobic bacteria are active, and that said gas circulation means has a circulation fan disposed in the midway of said air return pipe for circulating air in said processing vessel to said heat exchanger.

17. An apparatus for processing solid organic waste by crushing and/or agitating and fermenting the waste according to claim 11, characterized in that a waste discharge port is disposed in said upper processing vessel, an upper end plate being disposed in said upper processing vessel on the side thereof opposite to said waste charge port so that processed matters overflow said end plate and drop into said lower stage processing vessel, said lower processing vessel being formed shorter than said upper processing vessel while a lower end plate is disposed at one end of said lower processing vessel, a discharging matter storing unit having a length corresponding the difference between said upper stage processing vessel and said lower stage processing vessel being disposed below said upper stage processing vessel so that the processed matters which overflow the lower end plate of said lower stage processing vessel drop into said discharging matter storing unit, a rotary shaft, bearings and drive means for driving said rotary shaft being disposed regarding each of said upper and lower processing vessels arranged in the form of the two stages which rotary shaft is provided with agitation arms, and that fixed arms extending from the bottom of said upper stage vessel are disposed below the waste charge port of said upper stage processing vessel and between a plurality said agitation arms so that charged waste is crushed by said agitation arms and said fixed arms.

18. An apparatus for processing solid organic waste by crushing and/or agitating and fermenting the waste according to claim 11, characterized in that said gas circulation means is disposed in the midway of a path comprising said air intake pipe, said air return pipe and said heat exchanger connected to said air intake pipe and said air return pipe, said gas circulation means being provided with an air intake port for taking outside air, said deodorization processing unit being provided with a deodorizing communication pipe connected to said air return pipe located between said circulation fan and said processing vessel, an air exhaust pipe for exhausting a deodorized gas, a deodorizing vessel in which active sludge is sealed, a blow pipe for blowing air supplied from said deodorizing communication pipe into the active sludge and a pump so that air from the active sludge is exhausted into the atmosphere through said air exhaust pipe.

19. An apparatus for processing solid organic waste by crushing and/or agitating and fermenting the waste according to claim 11, characterized in that wherein an air intake pipe and an air return pipe are detachably connected to said processing vessel by connecting means; an auxiliary frame for supporting said processing vessel being formed separately from a main frame for supporting said heat exchanger, air supply means and deodorizing means to which auxiliary frame are connected all of rotary shafts of said upper stage and lower stage, bearings, a sprocket and a chain for connecting said upper rotary shaft to said lower rotary shaft, an insulation member, and a portion of an outside box so that said auxiliary frame and components connected thereto can be easily removed from said main frame when maintenance and service are carried out.

20. An apparatus for processing solid organic waste by crushing and/or agitating and fermenting the waste according to claim 11, characterized in that the agitation arms mounted on said rotary shaft are axially inclined in the range of 3°–45°.

21. An apparatus for processing solid organic waste by crushing and/or agitating and fermenting the waste according to claim 11, characterized in that an intermediate partition is disposed to at least one of the fermenting unit of said upper stage processing vessel and said lower processing vessel so that processed matters in said processing vessel overflow said intermediate partition and sequentially move to an adjacent region.

22. An apparatus for processing solid organic waste by crushing and/or agitating and fermenting the waste according to claim 1, further including a liquid purification unit for removing an organic matter from liquid condensed by said heat exchanger which unit neutralizes the liquid, a processing vessel of a liquid organic matter processing device being made to include aerobic bacteria filled therein and a heating means disposed on the outside wall surface of said vessel, and that each of said solid organic matter processing device, said heat exchanger and said deodorization processing unit is detachably arranged through a frame.

23. An apparatus for processing solid organic waste by crushing and/or agitating and fermenting the waste according to claim 1, characterized in that said solid organic matter processing device comprises rectangular box-shaped processing vessels each having a bottom portion connected in parallel at two curved bottom surfaces each having arc-shaped cross section, two rotary shafts disposed in the longitudinal direction of said processing vessels each of which shaft has a plurality of agitation arms fixed thereto, fixed arms planted on the wall surface of said processing vessel and not interfering with said agitation arms, and a partition plate for separating a crushing unit from a processing unit, each of the rotary shafts in said processing vessels being disposed at the center of the arc of the curved bottom surface, and that the position where said two curved bottom surfaces are connected is located below said rotary shafts while the partition plate forms a gap between it and the inside wall of said processing vessel.

24. An apparatus for processing solid organic waste by crushing and/or agitating and fermenting the waste according to claim 3, characterized in that a liquid purification unit of a gas and liquid processing unit includes an adjustment tank filled with a weak alkaline material and a processing tank connected to said adjustment tank which processing tank is filled with a carrier to which microorganisms are fixed so that liquid passing through said adjustment tank is neutralized thereby while the organic material of the liquid passing through said adjustment tank is removed thereby.

25. An apparatus for processing solid organic waste by crushing and/or agitating and fermenting the waste according to claim 3, wherein a deodorization processing unit of a gas and liquid processing unit has microorganisms for decomposing an odor and for deodorizing a gas by causing the gas to come into contact with the microorganisms.

26. An apparatus for processing solid organic waste by crushing and/or agitating and fermenting the waste according to claim 3, characterized in that a liquid purification unit comprises an adjustment tank filled with a weak alkaline material, a deodorizing tank filled with a liquid mixed with a carrier to which microorganisms are fixed and a water level tank having a discharge pipe disposed at the same position as the liquid surface of said deodorizing tank, said adjustment tank being connected to said deodorizing tank, said water level tank being connected to said deodorizing tank through a pipe at the lower portions thereof, and that the microorganisms fixed to the carrier in said deodorizing tank decompose both the odor of a gas introduced from said processing unit and the organic matter of liquid passing through said adjustment tank.

27. An apparatus for processing solid organic waste by crushing and/or agitating and fermenting the waste according to claim 1, characterized by further comprising a storage tank connected to the downstream side of said solid organic matter processing device through a connection pipe including a blower for storing processed and discharged matters, a water storage tank connected to a liquid purification unit through a connection pipe, and sprinkling means connected to said water storage tank through a water discharge pipe having a pump to thereby supply the processed and discharged matters and water to the surroundings of the location where said apparatus is installed.

28. An apparatus for processing solid organic waste by crushing and/or agitating and fermenting the waste according to claim 1, including a control unit for stopping the operation of said processing unit after a lapse of a predetermined period of time but continuously operating only said gas circulation means.

29. Apparatus for composting solid organic waste with supplying composting air, comprising:

a processing vessel having a top charging opening for the waste material which charging opening is provided at one end of the vessel, and crushing means for crushing, agitating and composting the waste material which crushing means is arranged beneath the charging opening;

a heat exchanger disposed outside of the vessel for condensing the water vapor contained in the composting air;

an air-circulation means for providing an air circulation path from the vessel to the heat exchanger and from the latter one back to the vessel;

a fresh-air inlet into the apparatus and an used air-outlet from the apparatus;

a storing unit for the compost which storing unit is arranged at the other end of the vessel; and conveyor means for moving the waste from the crushing unit through the vessel to the storing unit.

30. Apparatus for composting solid organic waste with supplying composting air, comprising:

a processing vessel having a top charging opening for the waste material which charging opening is provided at one end of the vessel, and crushing means for crushing, agitating and composting the waste material which crushing means is arranged beneath the charging opening;

a heat exchanger disposed outside of the vessel for condensing the water vapor contained in the composting air;

an air-circulation means for providing an air circulation path from the vessel to the heat exchanger and from the latter one back to the vessel;

a fresh-air inlet into the apparatus and an used air-outlet from the apparatus;

a storing unit for the compost which storing unit is arranged at the other end of the vessel;

conveyor means for moving the waste from the crushing unit through the vessel to the storing unit; and a control unit for stopping the operation of said processing unit after a lapse of a predetermined period of time but continuously operating only said air-circulation means.

* * * * *